(12) United States Patent
Hanson et al.

(10) Patent No.: US 6,635,060 B2
(45) Date of Patent: Oct. 21, 2003

(54) BONE PREPARATION INSTRUMENTS AND METHODS

(75) Inventors: David A. Hanson, Minneapolis, MN (US); Ross A. Longhini, Woodbury, MN (US); Steven J. Seme, Savage, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 0 days.

(21) Appl. No.: 09/896,926

(22) Filed: Jun. 28, 2001

(65) Prior Publication Data

US 2002/0068941 A1 Jun. 6, 2002

Related U.S. Application Data

(63) Continuation-in-part of application No. 09/611,237, filed on Jul. 6, 2000.

(51) Int. Cl.$^7$ ............................................. A61B 17/32
(52) U.S. Cl. ...................................................... 606/79
(58) Field of Search .......................... 606/79, 80, 85, 606/86, 96, 99, 108, 172, 183; 30/358, 299, 305, 315

(56) References Cited

U.S. PATENT DOCUMENTS

| | | | | |
|---|---|---|---|---|
| 1,913,800 A | * | 6/1933 | Farquhar | 30/305 |
| 2,818,070 A | * | 12/1957 | Barry | 604/46 |
| 3,783,860 A | * | 1/1974 | Burstein et al. | 606/62 |
| 3,848,601 A | | 11/1974 | Ma et al. | |
| 4,743,256 A | | 5/1988 | Brantigan | |
| 4,834,757 A | | 5/1989 | Brantigan | |
| 4,848,309 A | * | 7/1989 | Alderete | 125/40 |
| 4,877,020 A | | 10/1989 | Vich | |
| 4,878,915 A | | 11/1989 | Brantigan | |
| 5,015,247 A | | 5/1991 | Michelson | |
| 5,048,190 A | * | 9/1991 | Aurness et al. | 30/299 |
| 5,562,736 A | * | 10/1996 | Ray et al. | 606/61 |
| 5,571,109 A | | 11/1996 | Bertagnoli | |
| 5,609,636 A | | 3/1997 | Kohrs et al. | |
| 5,658,337 A | | 8/1997 | Kohrs et al. | |
| 5,722,977 A | | 3/1998 | Wilhelmy | |
| 6,059,790 A | | 5/2000 | Sand et al. | |
| 6,063,088 A | | 5/2000 | Winslow | |
| 6,066,174 A | | 5/2000 | Farris | |
| 6,083,225 A | * | 7/2000 | Winslow et al. | 606/61 |
| 6,197,033 B1 | * | 3/2001 | Haid et al. | 606/99 |
| 6,224,599 B1 | | 5/2001 | Baynham et al. | |
| 6,224,607 B1 | * | 5/2001 | Michelson | 606/96 |

FOREIGN PATENT DOCUMENTS

| | | |
|---|---|---|
| EP | 0 824 893 A2 | 2/1998 |
| EP | 0 880 938 A1 | 12/1998 |
| JP | 08126647 | 5/1996 |
| WO | WO 99/56676 | 11/1999 |

OTHER PUBLICATIONS

Branch, C., "Tangent, Posterior Discectomy & Grafting Instrumentation Set", Surgical Technique, Medtronic Sofamor Danek, 26 pages (1999).

* cited by examiner

Primary Examiner—Eduardo C. Robert
(74) Attorney, Agent, or Firm—Merchant & Gould PC

(57) ABSTRACT

Instruments and methods for preparing adjacent bones for fusion, and for inserting implants are disclosed. In one embodiment, the instruments include paddles for spacing the adjacent bones a predetermined distance and a cutting edge to create a channel between the adjacent bones to receive a fusion implant. In another embodiment, the instruments include a bone cutting instrument, a rasp, and an implant inserting tool. The instruments and methods are particularly advantageous for preparing a spinal fusion implant site.

9 Claims, 17 Drawing Sheets

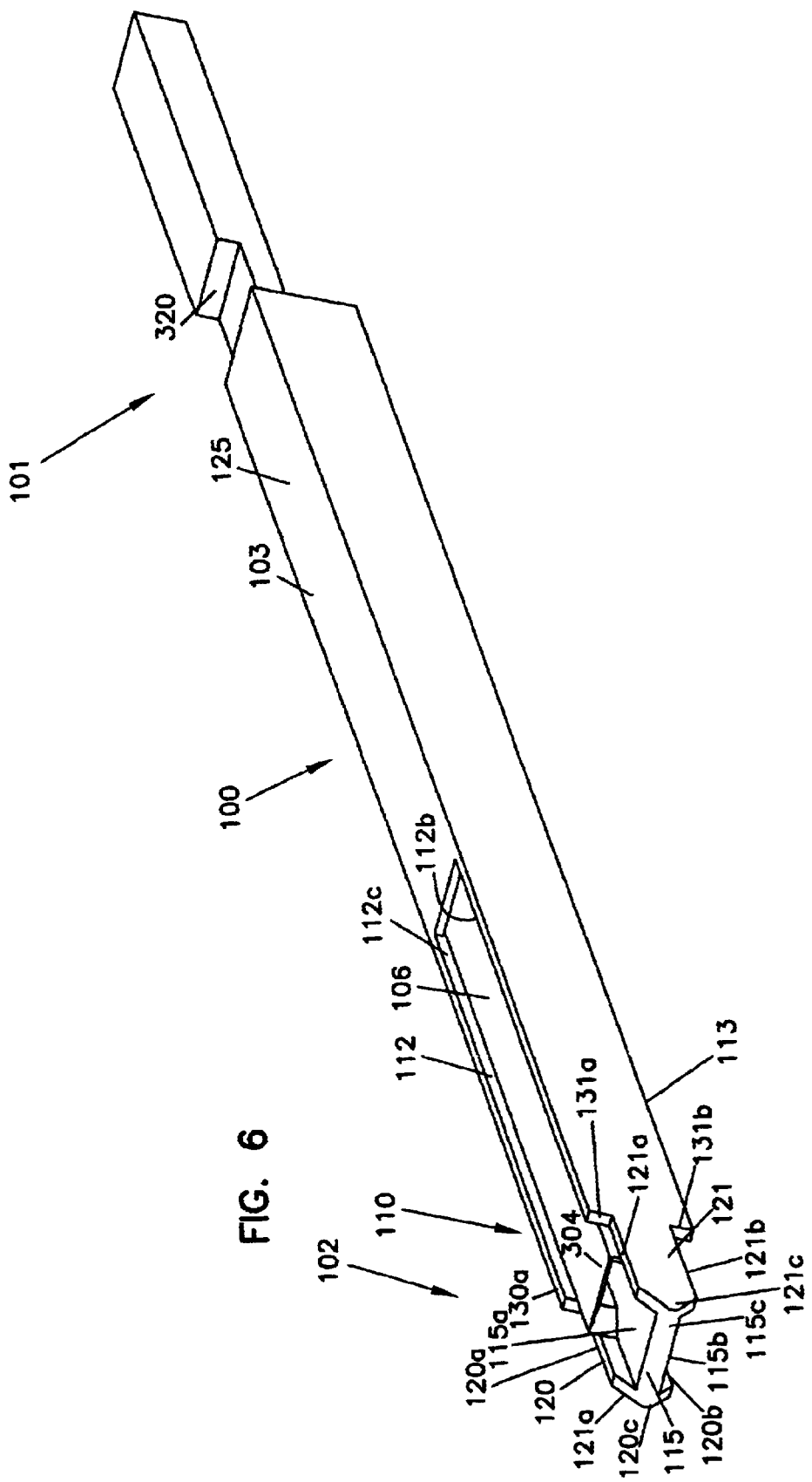

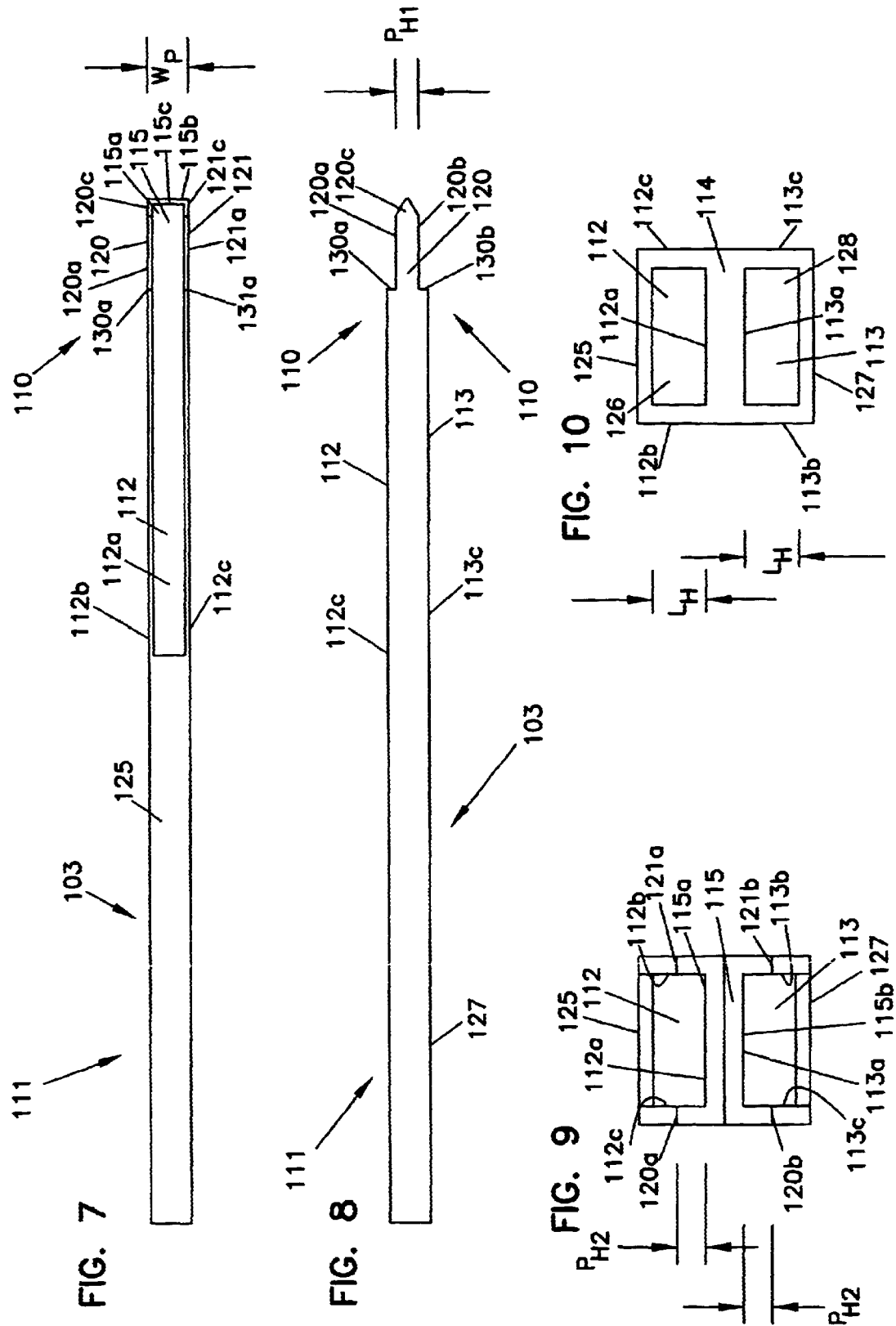

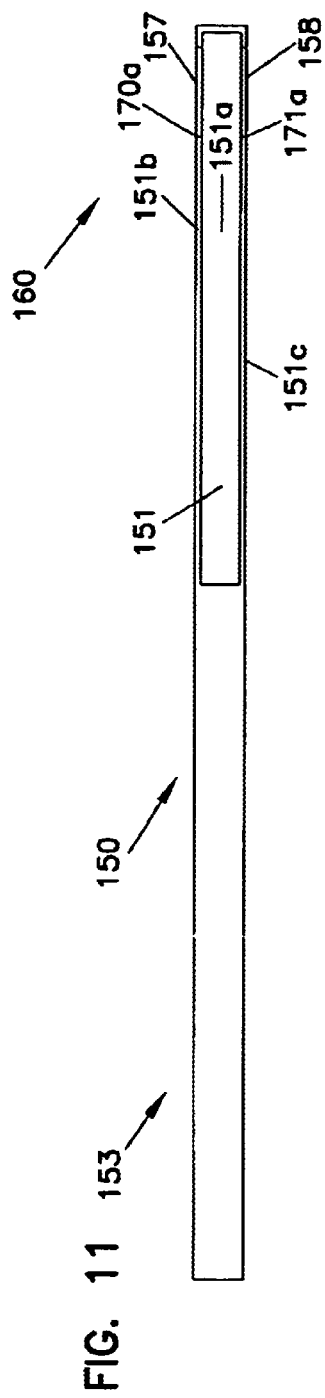
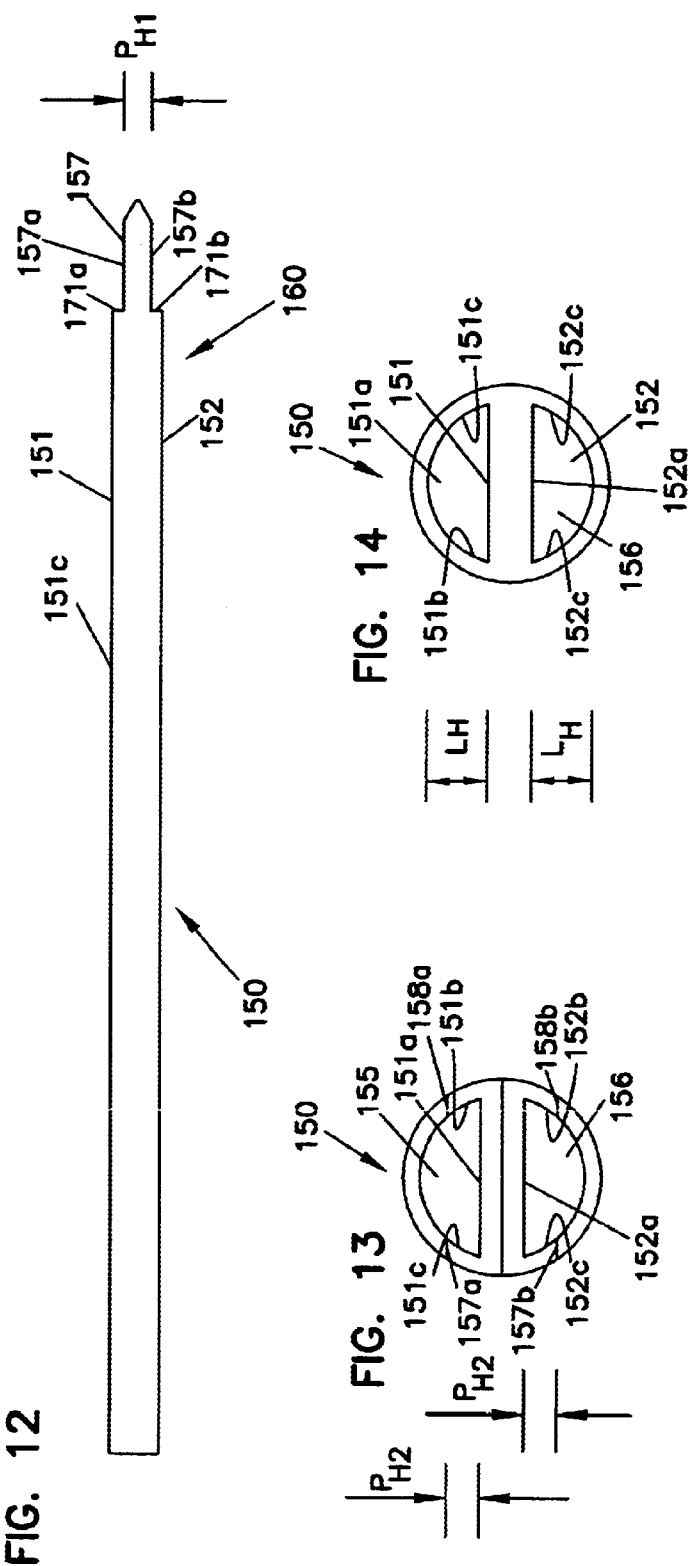

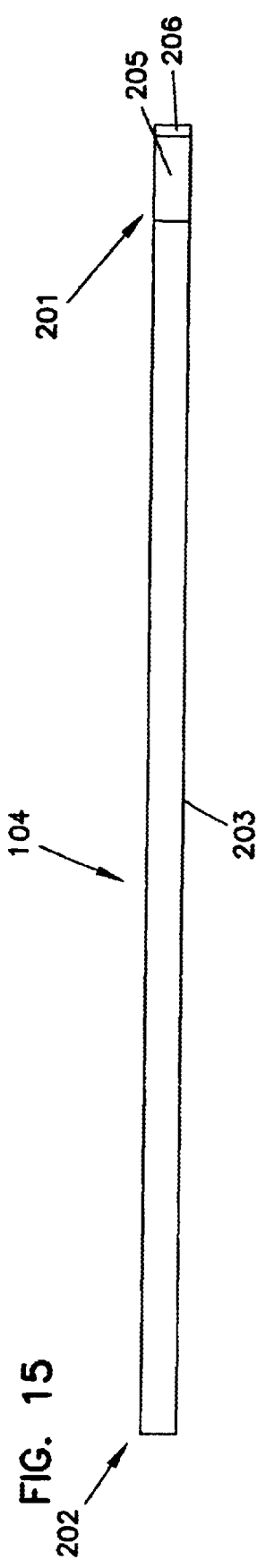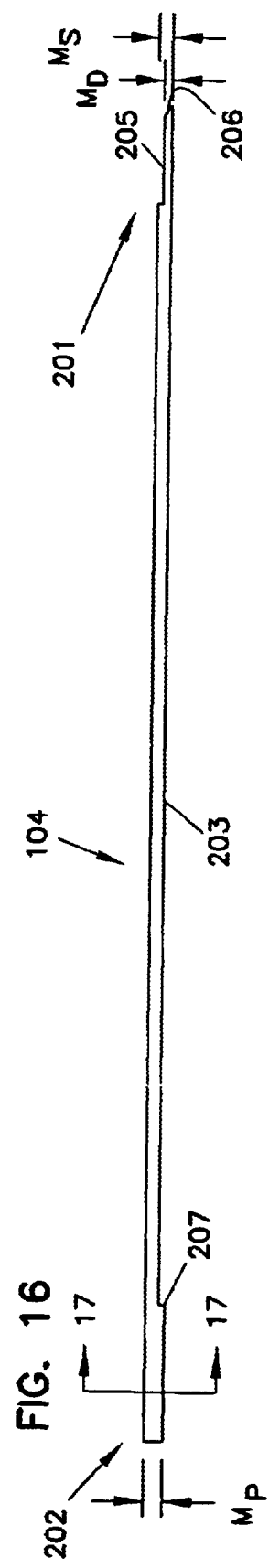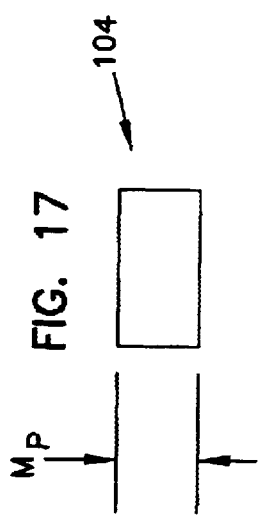

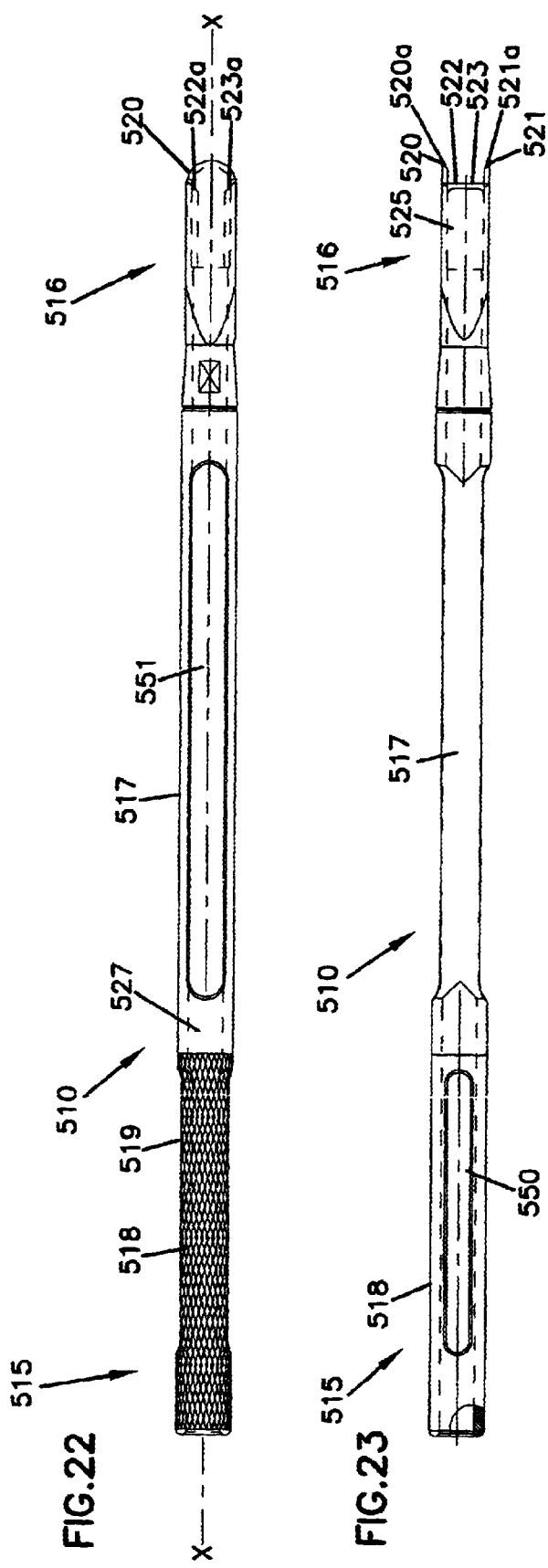
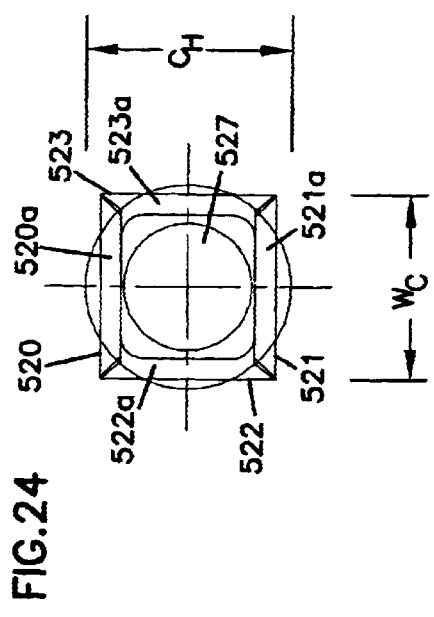

BONE PREPARATION INSTRUMENTS AND METHODS

The present application is a continuation-in-part of Ser. No. 09/611,237 filed Jul. 6, 2000.

FIELD OF THE INVENTION

This invention pertains to bone surgery. Specifically, the invention is directed to instrumentation and methods for preparing adjacent bones for receiving an implant therebetween. The invention is particularly advantageous for preparing an implant site for fusing vertebral bodies to facilitate fusion.

BACKGROUND OF THE INVENTION

Chronic back problems can cause pain and disability for a large segment of the population. Frequently, the cause of back pain is traceable to diseased disc material between opposing vertebrae. When the disc material is diseased, the opposing vertebrae may be inadequately supported, resulting in persistent pain.

Surgical techniques have been developed to remove the diseased disc material and fuse the joint between opposing vertebral bodies. Arthrodesis or fusion of the intervertebral joint can reduce the pain associated with movement of an intervertebral joint having diseased disc material. Generally, fusion techniques involve removal of the diseased disc and inserting a bone or non-bone implant between the opposing vertebral bodies to be fused.

Spinal fusion implants and related surgical instruments for implanting a fusion device are known and disclosed in, for example, U.S. Pat. Nos. 5,741,253; 5,722,977; 5,658,337; 5,609,636; 5,505,732; 5,489,308; 5,489,307; 5,458,638; 5,055,104; 5,026,373; 5,015,247; 4,961,740; 4,878,915; 4,834,757; 4,743,256; 4,501,269; and 3,848,601. The disclosure of each of these patents is incorporated herein by reference.

Often times, the degenerative changes of the diseased disc cause a collapse of the intervertebral disc space. Thus, prior to implantation, the intervertebral disc space may be distracted to restore the normal height of the disc space or the normal relationship between the vertebrae to be fused. Maintaining the restored disc space height and/or vertebral relationships throughout preparation of the implant site can be important for the ultimate stability at the fusion site.

The ease of use and efficiency of instruments and procedures used to prepare and place an implant at a fusion site is also very important to the overall success of the procedure. For example, in addition to other problems, removal of unequal amounts of bone on either side of the fusion site, particularly in vertebral fusion procedures, can result in over reaming of one vertebra relative to the adjacent vertebra and ultimately lead to a poorer surgical outcome.

Accordingly, there is a continuing need for instrumentation and methods that ensure precise placement of the implant as well as increasing the ease and efficiency of the implant procedure. The present invention is directed to this need.

SUMMARY OF THE INVENTION

The present invention is directed to bone cutting instruments and methods that provide efficient and precise preparation of a bore for receiving an implant between adjacent bones that are to be fused.

Throughout the specification, guidance may be provided through lists of examples. In each instance, the recited list serves only as a representative group. It is not meant, however, that the list is exclusive.

In one embodiment, the instruments of the invention include bone cutting instruments having paddles that can be inserted between adjacent bones to maintain a fixed spacing between the bones during preparation of the bones for fusion. In one embodiment, the bone cutting instruments include a cutting edge that is fixedly mounted to the spacing paddles. In an alternative embodiment, the paddles can be mounted to a channel guide that provides a track for slidably positioning the cutting edge at the site of bone preparation.

In a typical embodiment, a bone cutting instrument includes a cutting edge that extends beyond the height dimensions of the paddles with a portion of the cutting edge extending between the paddles. Depending on the configuration of the implant to be inserted between bones, the cutting edge can be circular, oval, rectangular, etc.

In another embodiment, a bone cutting instrument includes first, second, third, and fourth cutting edges that define an interior void, with the first and second cutting edges being opposite and extending beyond the third and fourth cutting edges.

In a further embodiment, the invention involves a rasp adapted to define a recess between two bone surfaces. The rasp includes a shaft and a rasp head with an arcuate distal surface. At least one of the transverse surfaces of the rasp is roughened. Examples of roughened surfaces include knurls, etchings, ridges, grooves, teeth, etc.

In a still further embodiment, the invention involves an implant insertion tool having a shaft with a pair of arms movable between a spaced apart holding position and a close together releasing position. The distal ends of the arms are shaped to fit inside an implant. The insertion tool also involves a sleeve operable on the arms to force the arms together towards the releasing position. The sleeve is hollow and is slidably mounted on the shaft. The sleeve forces the arms together to release the implant when the sleeve is in the engaging position. In an alternative embodiment, the sleeve is internally threaded and the shaft is externally threaded, with the threads matching. In this embodiment, the sleeve is rotated to move it along the shaft. The invention also provides kits comprising one or more instruments of the invention having various paddle and/or cutting edge heights, widths or shapes for preparing an implant site of a predetermined size or shape.

BRIEF DESCRIPTION OF THE DRAWINGS

FIG. 6 is a view of the same bone cutting instrument of FIG. 5 with the first and second mandrels removed and a bone chisel in the place of the first mandrel.

FIG. 7 is a top plan view of the channel guide of FIG. 5 (the opposite side being substantially identical).

FIG. 8 is a side view of the channel guide of FIG. 7 (the opposite side view being substantially identical).

FIG. 9 is a distal end view of the channel guide of FIG. 7.

FIG. 10 is a proximal end-on view of the channel guide of FIG. 7.

FIG. 11 is a top plan view of an alternative embodiment of a channel guide according to the invention.

FIG. 12 is a side plan view of the channel guide of FIG. 11.

FIG. 13 is a distal end-on view of the channel guide of FIG. 11.

FIG. 14 is a proximal end-on view of the channel guide of FIG. 11.

FIG. 15 is a top plan view of one embodiment of a mandrel according to the invention.

FIG. 16 is a side plan view of the mandrel of FIG. 15.

FIG. 17 is a transverse cross-section view of the mandrel of FIG. 15 through line 16—16.

FIG. 22 is a top view of another embodiment of a bone cutting instrument according to the invention.

FIG. 23 is a side view of the bone cutting instrument of FIG. 22.

FIG. 24 is a distal end-on view of the bone cutting instrument of FIG. 22.

DETAILED DESCRIPTION OF THE INVENTION

Figure 1:
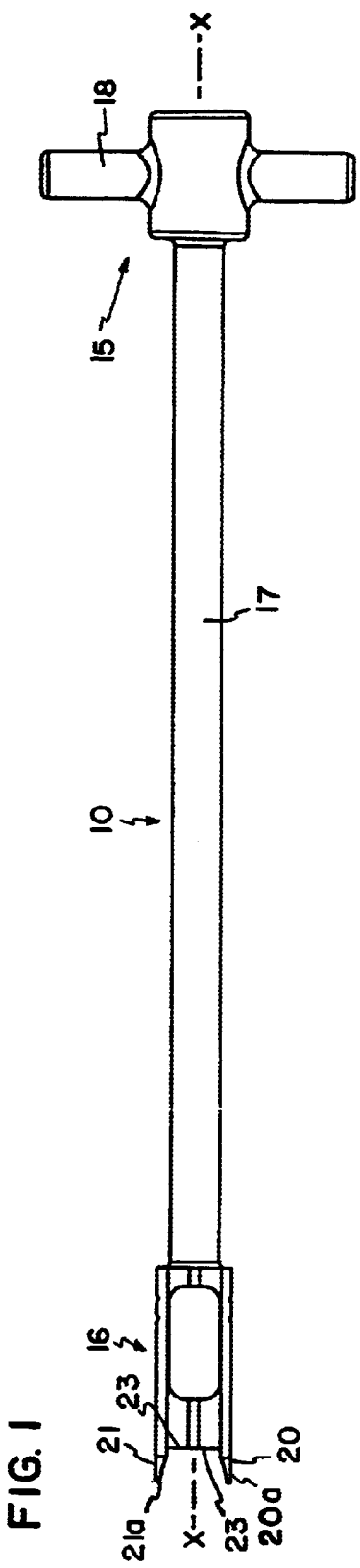
FIG. 1 is a side view of one embodiment of a bone cutting instrument according to the invention.

The present invention is directed to instruments and methods for preparing an implant site for receiving an implant between adjacent bones to be fused. The instruments of the invention can be advantageously used for fusion of joints. In some embodiments, the instruments and methods disclosed are particularly advantageous for preparing an implant site for fusing cervical, thoracic and/or lumbar intervertebral joints. Thus, for exemplary purposes, the instruments and methods of the invention will be described with reference to fusion of a lumbar intervertebral joint. However, it will be appreciated that the disclosed instruments and methods can be used for fusion of all types of bones and particularly bones adjacent to a joint space. In the case of fusing an intervertebral joint, the invention can be performed using an anterior, posterior or lateral approach to the patient's vertebrae.

As used herein, an "implant" includes any implant suitable for facilitating fusion between adjacent bones and includes implants prepared from known implant materials including, non-bone material such as titanium, stainless steel, porous titanium, ceramic, etc. or bone including heterologous, homologous, autologous, artificial bone, etc. The implants suitable for the invention also can be threaded implants or non-threaded.

An "implant site" refers to the location for placement of an implant between adjacent bones, such as adjacent vertebrae. In a typical embodiment for vertebral fusion, the implant site can be a channel prepared by removing a notch from the opposing end plates of first and second vertebral bodies adjacent the intervertebral joint space. Preferably the notches are made through the articular cartilage and cortical bone into the cancellous bone. It will be appreciated that the notches formed in the bone can be any shape suitable for receiving an implant of a particular shape including, for example, rectangular, circular, oval, etc. In the case of a circular channel, after forming the channel, the channel can be threaded, using known tap systems, for receiving a threaded implant.

Preparing an implant site according to the invention can be performed more quickly and easily than prior procedures and can significantly reduce surgery time and costs. Some cutting tools previously used to prepare implant sites are easy to use but lack certain precision characteristics. For example, the distal end of some cutting tools may be vulnerable to shifting from a desired location during cutting due to a lack of vertical stability, caused by, for example, irregularities or undulations at the surface of the vertebrae against which the distal end of the cutting tool is placed during cutting.

The disclosed devices can provide greater vertical stability and, in the case of vertebral fusion, help to ensure that an equal amount of bone is removed from the endplates of the vertebrae on either side of the joint space. Removing equal amounts of bone can facilitate greater coaptation between the implant and the implant channel, greater fusion stability, greater motion segment stability, faster fusion, reduced pain, reduced chance of migration, reduced chance of subsidence, etc.

Throughout the specification, unless stated otherwise, the terms "proximal" and "distal" are relative terms, the term "proximal" referring to a location nearest the surgeon and the term "distal" referring to a location farthest from the surgeon. So, in the case of performing a vertebral fusion from an anterior approach, the anterior surfaces of the vertebrae are "proximal" and the posterior surfaces of the vertebrae are "distal" relative to the surgeon performing the procedure. Likewise, in a posterior approach, the posterior vertebral surfaces are proximal and the anterior surfaces are distal.

Generally, when preparing an implant site instruments used to prepare the site are advanced into the disc space from a proximal to distal direction. That is, in an anterior approach the instruments are advanced from the anterior surface (proximal) towards the posterior surface (distal) and in a posterior approach the instruments are advanced from the posterior surface (proximal) towards the anterior surface (distal). Similar relative orientations also apply for lateral approaches.

As used herein, the "depth" of a vertebra is defined as the anterior posterior dimension of the vertebrae. The "width" of the vertebrae is the dimension from the right lateral edge to the left lateral edge. The "height" of the disc space is the dimension from the superior endplate to the inferior endplate of opposing vertebrae.

The implants can be sized for a particular application. For example, for stabilizing a lumbar disc space, the implant may have a height dimension "H" of about 2 mm to about 30 mm, a width dimension "W" of about 6 mm to about 40 mm and a length dimension "L" of about 10 mm to about 40 mm. Other sizes will be appreciated as being within the scope of the invention after review of the present disclosure. One instrument of the invention, a bone cutting instrument or channel guide, has a proximal end and a distal end with a pair of paddles extending from the distal end of the instrument. In use, the paddles are placed into the space between the bones to be fused to provide vertical stability of the device as well to maintain a selected spacing between the bones, which is determined by the height of the paddles.

In general, the instruments will be available having varied paddle heights and varied widths between paddles. For cervical vertebral applications a typical range of paddle heights can be approximately 2 mm to 12 mm, in 1 mm increments. For lumbar applications a typical range of paddle heights can be approximately 3 mm to 18 mm in 1 mm increments. However, larger or smaller widths with larger or smaller increments can be available as needed. Thus, for example, in the case of vertebral fusion, a range of paddle heights will be available to establish and maintain a selected joint space height between the vertebrae during preparation of the implant site.

Instruments having various widths or spacing between paddles will be available for different procedures. For example, if a single implant is to be used, it will typically have a greater width, and thus require a preparation instrument having a greater spacing between paddles, than if multiple implants will be used. A typical width between paddles for a bone cutting instrument for placing a single implant can be about 4 mm to 40 mm. A typical width between paddles for a bone cutting instrument for implanting two implants between lumbar vertebrae will be about 4 mm to 24 mm.

The distal tip of the paddles can be tapered to facilitate insertion of the paddles into the joint space. In addition, the opposing edges of the paddles can have a convergent or divergent taper from the distal tip to a proximal aspect of the paddle. A tapered paddle can provide a lordotic taper to the joint space to create a channel for receiving a tapered implant for restoring or creating a particular degree of lordosis between the adjacent vertebral bodies.

A bone cutting instrument of the invention also includes a cutting edge. As will be further described below, the cutting edge can be separable or non-separable from the paddles. In the case of a separable cutting edge, the instrument can include one or more tracks to guide the cutting edge to a particular location. The cutting edge can be rectangular or circular, oval, elliptical, oblong, etc. In one embodiment, the cutting edge is a three-sided rectangle and provides for removing a rectangular notch of bone.

The invention can be used with known starter guides, depth gauges, taps and implant drivers used for preparing or inserting an implant into an implant site. Examples of suitable instruments are disclosed in U.S. Pat. Nos. 5,722,977; 5,658,337; 5,609,636; 5,489,307; 5,484,638; 4,834,757; 3,848,601, etc., the entire disclosures of which are incorporated herein by reference.

In another embodiment, instruments for preparing a channel in adjacent bones and for inserting an implant are sized to be used with a particular sized implant or implants. In this embodiment, each different size of implant has a corresponding set of bone cutting and implant inserting instruments. The instruments of the invention can be provided in kits including guides having paddles of different lengths and widths and correspondingly sized bone cutting edges for spacing bones and preparing implant sites for implants of various shapes and sizes. In another embodiment, the bone cutting instrument, rasp, and implant insertion tool can be provided in a kit, with or without an implant sized and configured to be implanted using the instruments. In a further embodiment, a kit can be provided that includes a plurality of incrementally sized implants and incrementally sized bone cutting instruments, rasps, and implant insertion tools so the user can select the appropriate size needed for a particular procedure.

DETAILED DESCRIPTION OF THE ILLUSTRATED EMBODIMENT

I. Instruments

The instruments and methods of the invention will now be described by reference to the accompanying drawings. The illustrated embodiments and description are provided only for exemplary purposes to facilitate comprehension of the invention and should not be construed to limit the scope of the invention.

Figure 2:
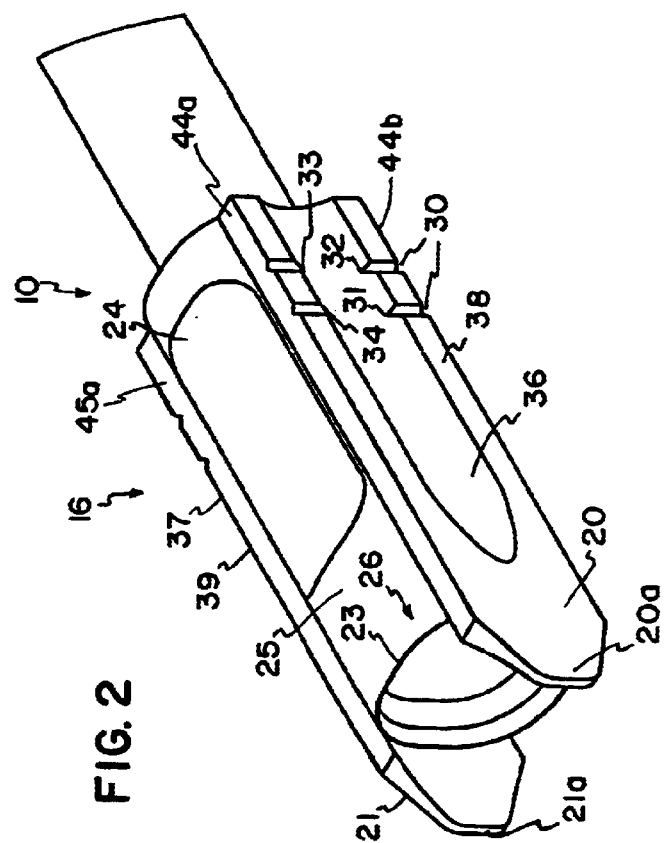
FIG. 2 is a close-up perspective view of the distal end of the bone cutting instrument of FIG. 1.

FIG. 1 is a side view and FIG. 2 an enlarged perspective view of the distal end of one embodiment of a bone cutting instrument 10 according to the invention. Instrument 10 has a proximal end 15 and a distal end 16 spaced along longitudinal axis X—X. At the proximal end 15 of shaft 17 there is a handle 18 for operating instrument 10. At the distal end 16, instrument 10 includes a first paddle 20, a second paddle 21 and a cutting edge 23. In the illustrated embodiment, cutting edge 23 is at the distal end of chamber 25. Proximal to cutting edge 23, chamber 25 can include one or more openings 24 for passage of bone debris collected within chamber 25 during cutting.

Paddles 20 and 21 include a tapered distal tip, 20a and 21a, respectively, to facilitate insertion of instrument 10 between adjacent bones. Proximal to the tapered distal ends 20a and 21a, instrument 10 also includes markings 30 such as notches 31–34 at predetermined distances from distal tips 20a and 21a. During use, markings 30 provide the surgeon with an indication of the depth of distal penetration of instrument 10 between adjacent bones. Furrows 36 and 37 (not visible) are present along a portion of the sides 40 and 41, respectively, of paddles 20 and 21. Furrows 36 and 37 provide a reduced surface area of paddle sides 38 and 39 and thus facilitate removal of instrument 10 from between adjacent bones.

Figure 3:
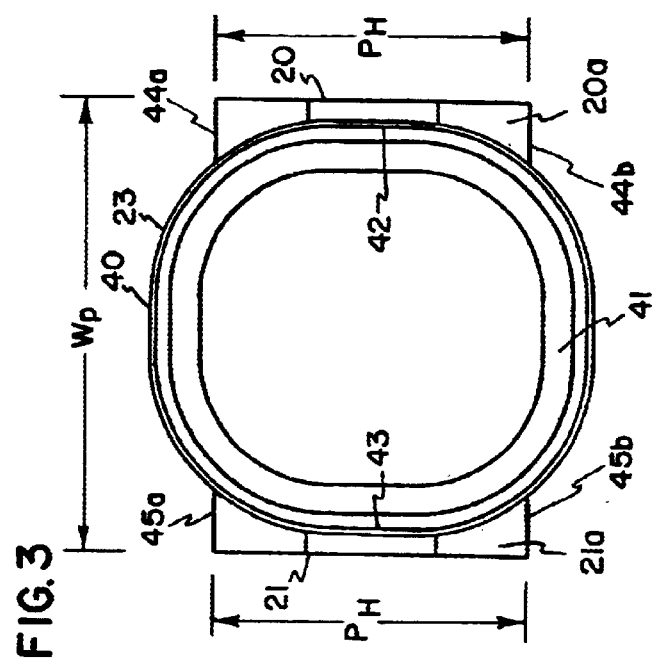
FIG. 3 is a distal end-on view of the bone cutting instrument of FIG. 1.
Figure 4:
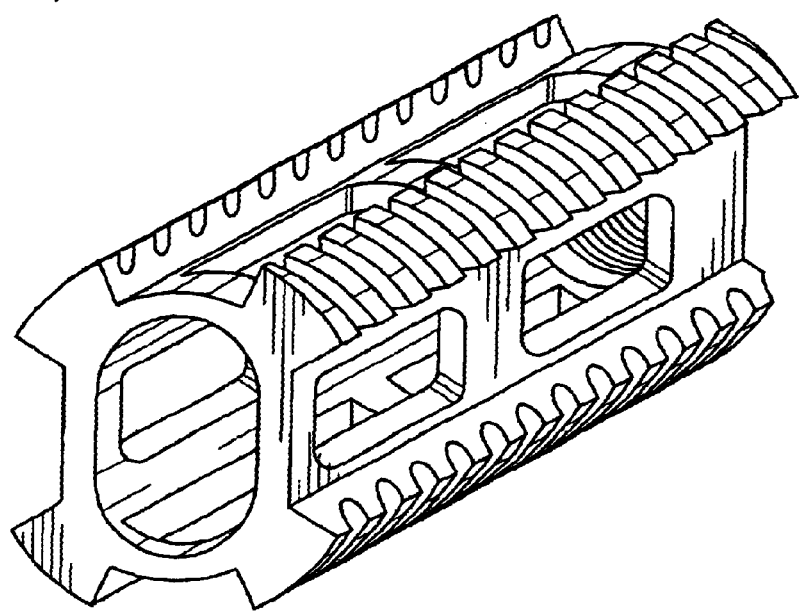
FIG. 4 is a perspective view of one embodiment of a non-bone implant suitable for use according to the invention.

FIG. 3 is a distal end-on view of instrument 10 showing that paddles 20 and 21 each have the same height dimension $P_H$ and a width dimension $W_P$ between paddles 20 and 21. A portion of cutting edge 23 is shown to extend beyond height dimension $P_H$ at location 40 and 41 and a portion of cutting edge 23 is within the spacing between paddles 20 and 21 at locations 42 and 43. The perimeter configuration of cutting edge 23 in FIG. 3 is a parallelepiped shape particularly suited for preparing a channel or implant bore between adjacent bones for insertion of an implant having a cross-sectional configuration such as that of the implant shown in FIG. 4. It will be appreciated, however, that the perimeter configuration of cutting edge 23 can be square, rectangular, circular, oval, etc., depending on the external configuration of the implant to be inserted into the channel. In the illustrated embodiment, paddles 20 and 21 are fixedly attached to cutting edge 23. The paddle length can vary to correspond with the depth of the vertebrae.

For any particular perimeter configuration, bone cutting instruments 10 will be available which have incrementally varied sizes of cutting edge 23 corresponding to a particular size implant. In addition, bone cutting instruments 10 having paddles with varied heights $P_H$ will be available to permit the surgeon to select a paddle height corresponding to a particular disc space height. In addition, it will be appreciated that the illustrated paddle edges 44a, 44b (and 45a, 45b) are parallel. In alternative embodiments, edges 44a, 44b (and 45a, 45b) can form a converging or diverging taper.

Figure 5:
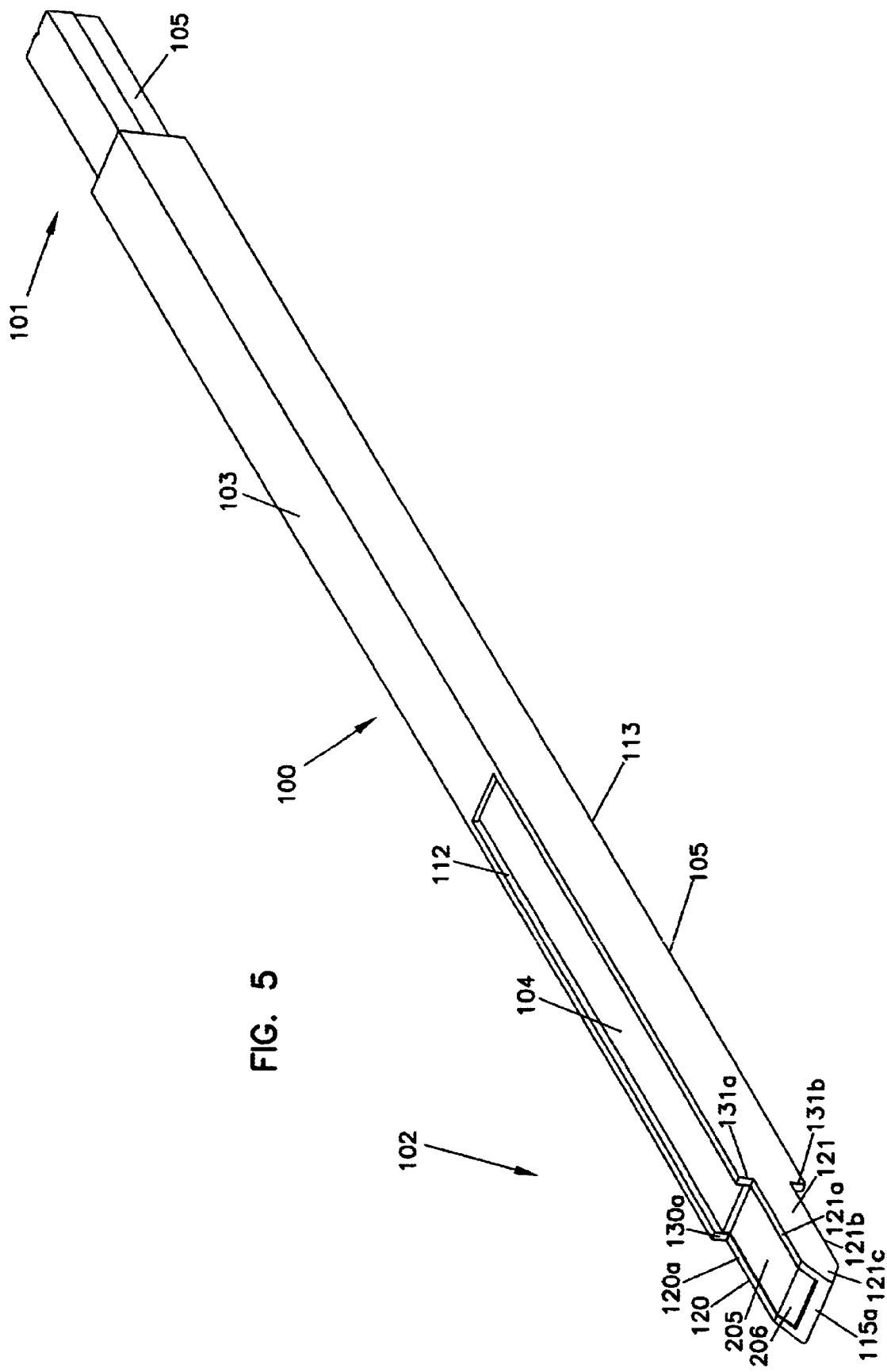
FIG. 5 is a perspective of an alternative embodiment of a bone cutting instrument according to the invention, including a channel guide and first and second mandrels.

FIG. 5 is a perspective view of an alternative embodiment of a bone cutting instrument 100. According to this embodiment, bone cutting instrument 100 has a proximal end 101, a distal end 102 and includes a channel guide 103, first mandrel 104 slidably received within a first track 112 and a second mandrel 105 slidably received within a second track 113. FIG. 6 illustrates bone cutting instrument 100 with first and second mandrels 104, 105 removed from tracks 112 and 113 of channel guide 103, and a bone chisel 106 slidably passed into track 112.

FIG. 7 is a top plan view of the channel guide 103, FIG. 8 is a side view, FIG. 9 is a distal end-on view and FIG. 10 is a proximal end-on view. Channel guide 103 includes a distal end 110, a proximal end 111 and a first track 112 and a second track 113 extending from the proximal end 111 to the distal end 110. Track 112 includes a base 112a, a first rail 112b and a second rail 112c. Track 113 includes a base 113a, a first rail 113b and a second rail 113c. In the illustrated embodiment, base 112a of track 112 and base 113a of track 113 are on opposing surfaces of rail spacing member 114.

Extending distally from distal end 110, channel guide 103 includes a first paddle 120 and a second paddle 121. Paddle 120 has a first edge 120a, a second edge 120b and a tapered distal end 120c. Likewise, paddle 121 has a first edge 121a, a second edge 121b and a tapered distal end 121c. Paddle spacing member 115 extends between paddles 120 and 121 and has a first base surface 115a continuous with base 112a of track 112, a second base surface 115b continuous with base 113a of track 113 and a tapered distal tip 115c coterminus with tapered distal ends 120c and 121c. Paddles 120 and 121 also have a width dimension $W_P$ therebetween, spaced apart by a width of spacing member 115. Tapered distal tips 115c, 120c and 121c facilitate insertion of the paddles between adjacent bones.

Paddle 120 has a major height dimension $P_{H1}$ between edge 120a and 120b. Paddle 120 also has a minor height dimension $P_{H2}$ between base surface 115a and edge 120a and an equal minor height dimension $P_{H2}$ between base surface 115b and edge 120b. Paddle 121 has the same height dimensions $P_{H1}$ and $P_{H2}$ as paddle 120.

In the illustrated embodiment, a portion of track 112 includes a wall 125 extending between rails 112b and 112c and parallel to base 112a. Shown best in FIG. 10, wall 125 extending between rails 112b and 112c forms an enclosed lumen 126 over a proximal portion of track 112. In a similar manner, a portion of track 113 includes a wall 127 extending between rails 113b and 113c which forms enclosed lumen 128 in that portion of track 113 where wall 127 is present. Each of lumens 126 and 128 has a height dimension $L_H$. As best seen in FIG. 10, if walls 125 and 127 are ignored, and channel guide 103 viewed from the proximal end with rail spacing member 114 oriented in a vertical plane, channel guide 103 can have an "I beam" shaped configuration.

At the junction of the distal end 110 of channel guide 103 with paddles 120 and 121, shoulders 130a, 130b and 131a, 131b are formed. Shoulders 130a–131b provide an affirmative stop to stop distal advancement of bone cutting instrument 100 when paddles 120 and 121 are inserted into an intervertebral disc space between adjacent vertebrae.

FIGS. 11–14 illustrate an alternative embodiment of a channel guide 150 according to the invention. Channel guide 150 is substantially identical to channel guide 103 except that channel guide 150 has a circular cross-section. However, similar to channel guide 103, channel guide 150 includes a first track 151 and a second track 152. Track 151 includes a base 151a, a first rail 151b and a second rail 151c. Likewise, track 152 includes a base 152a, a first rail 152b and a second rail 152c. Extending a portion of the length of channel guide 150 from proximal end 153, rails 151b and 151c are continuous with one another forming an enclosed lumen 155 over track 151. A similar enclosed lumen 156 is present over track 152. Each of hemi-circular lumens 155 and 156 has a maximum lumen height $L_H$.

Paddles 157 and 158 extend distally from the distal end 160 of tracks 151 and 152 respectively. Paddles 157 and 158 have a curved cross-section and each has a major height dimension $P_{H1}$ extending from edge 157a to edge 157b and from edge 158a to edge 158b. Each of paddles 157 and 158 have a first and second minor height dimension $P_{H2}$ as described for channel guide 103. Shoulders 170a 170b are formed at the junction of distal end 160 and paddles 157 and shoulders 171a and 171b are formed at the junction of distal end 160 and paddle 158. It will be appreciated that various cross-sectional configurations for channel guides are within the scope of the invention, in addition to the rectangular cross-section of channel guide 103 and the circular cross-section of channel guide 150.

FIG. 15 is a top plan view of mandrel 104 (105 being identical) shown in FIG. 5; FIG. 16 is side plan view of mandrel 104 and FIG. 17 is a transverse cross-section view of mandrel 104 taken through line 16—16. Mandrel 104 includes a distal end 201, a proximal end 202 and a shaft 203 extending therebetween. As best seen in FIG. 15, mandrel 104 has a gap surface 205 and a tapered distal tip 206 at distal end 201. Mandrel 104 has a shaft height $M_S$ along a portion of shaft 203, a distal end height $M_D$ at distal end 201 and a proximal end height $M_P$ at proximal end 202. Preferably, distal end height $M_D$ is substantially equal to minor height $P_{H2}$ of paddles 120 and 121. Thus, when height $M_D$ of mandrel 104 is equal to minor height $P_{H2}$ of paddles 120 and 121, a flush surface is provided extending from edge 120a of paddle 120 across gap surface 205 and edge 121a of paddle 121 (see FIG. 5). A similar flush surface is formed between mandrel 105 and paddle edges 120b and 121b.

With mandrels 104 and 105 inserted within tracks 112 and 113 the space between paddles 120 and 121 is filled out. Thus, when inserted into an intervertebral disc space, pressure exerted by the bone cutting instrument 100 on each of the opposing vertebrae is not localized only on the edges of the paddles, but rather the pressure is distributed across the entire surface area between the paddles and including the gap surfaces of the mandrels. It will be appreciated that if the distracting guide has a cylindrical cross-section as illustrated in, for example, FIG. 11, the mandrel will have a corresponding shape including the features described for rectangular shaped mandrel 104 and 105.

Shaft height $M_S$ of mandrel 104 is provided to pass within track height $L_H$ in close tolerance within lumen 126 (or 128) of channel guide 103. The proximal end height $M_P$ of mandrel 105 at the proximal end 202 is selected to be greater than shaft height $M_S$ of shaft 203 to form a shoulder 207. Shoulder 207 affirmatively stops distal advancement of mandrel 104 along track 112 when shoulder 207 abuts rail spacing member 114 of channel guide 103. Second mandrel 105 can be configured identical to mandrel 104 to pass into track 113 and from base surface 115b to edges 120b and 121b.

In a typical embodiment, paddle major height dimension $P_{H1}$ can be about 3 to 15 mm, paddle minor height dimension $P_{H2}$ about 1 to 7 mm, lumen height dimension $L_H$ about 2 to 13 mm and mandrel proximal height dimension $M_P$ of about 1 to 2 mm greater than lumen height dimension $L_H$. For example, in the illustrated embodiment 100, the paddle major height dimension can be $P_{H1}$ is 8 mm, the paddle minor dimension $P_{H2}$ can be about 3.5 mm, the lumen height dimension $L_H$ 5 mm and the mandrel proximal height dimension about $M_P$ 6 mm.

Figure 19:
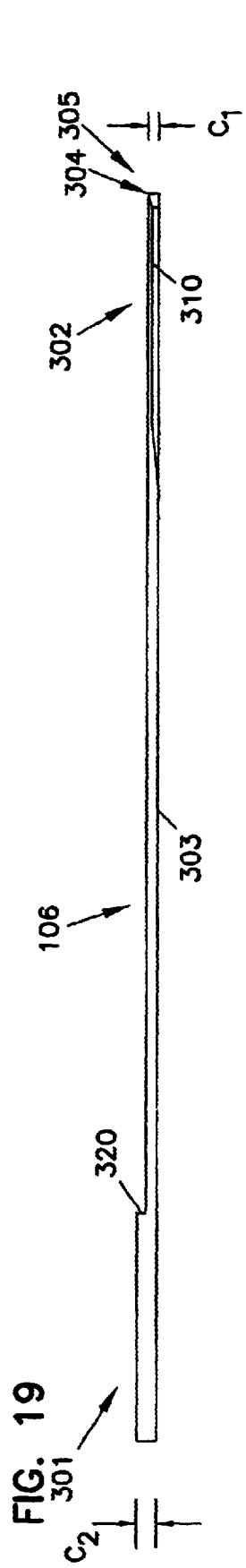
FIG. 19 is a longitudinal cross-section view taken through line 18—18 of the bone chisel of FIG. 18.
Figure 18:
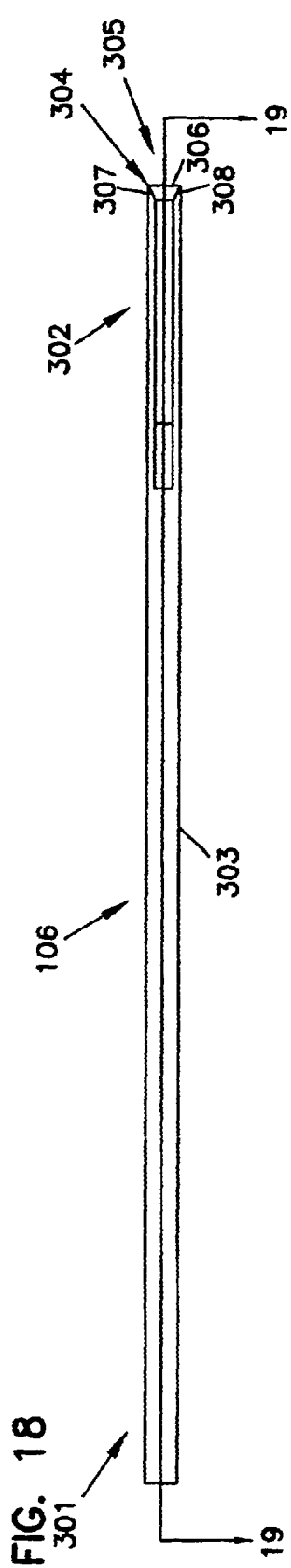
FIG. 18 is a top plan view of one embodiment of a bone chisel according to the invention.
Figure 20:
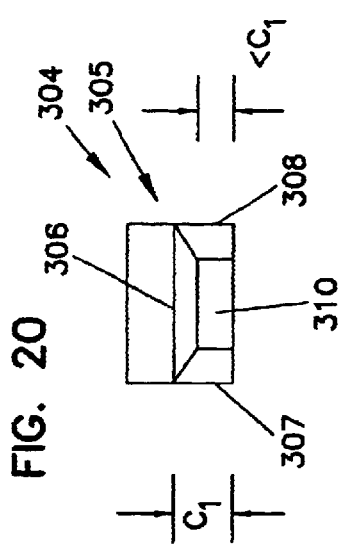
FIG. 20 is a distal end view of the bone chisel of FIG. 18.

FIG. 18 is a top plan view of one embodiment of a bone chisel 106 shown in FIG. 6. FIG. 19 is a longitudinal cross-section view through line 19—19, and FIG. 20 is a distal end-on view of bone chisel 106. Bone chisel 106 includes a proximal end 301, distal end 302 and shaft 303 therebetween. Cutting surface 304 is at distal end 302. Cutting surface 304 is a rectangular cutting surface 305 including longitudinal cutting edge 306 and first lateral cutting edge 307 and second lateral cutting edge 308.

Distal end 302 of chisel 106 has a first chisel height $C_1$. In a typical embodiment, the difference between first chisel height $C_1$ and paddle minor dimension $P_{H2}$ determines the amount of bone removed from a bone end during bone cutting. Thus, to remove about 1 mm of bone from the end of the bone, the difference between $C_1$ and $P_{H2}$ is about 1 mm. $C_1$ is typically selected to be about 1 to 3 mm greater than paddle minor dimension $P_{H2}$. In the case of cutting bone from vertebral endplates, $C_1$ is preferably sufficient to cut deep enough into the endplate to remove the articular cartilage and cortical bone to expose cancellous bone.

The distal end 302 of bone chisel 106 also includes a groove 310 extending a distance proximally from cutting surface 304 between cutting edges 306–308. As illustrated in the longitudinal cross-section view of FIG. 19, groove 310 has a depth less than chisel height $C_1$ and provides for proximal passage of bone, cartilage or other debris as chisel 106 is advanced distally to cut between adjacent bones.

At proximal end 301, bone chisel 106 has a second chisel height $C_2$. A shoulder 320 is formed where chisel heights $C_1$ and $C_2$ meet. Chisel height $C_1$ is selected to provide for bone chisel 106 to pass in close tolerance within lumen 126 (or 128) of channel guide 103. Shoulder 320 affirmatively stops distal advancement of bone chisel 106 within tracks 112 or 113 when shoulder 320 abuts against wall 125 or 127 at the proximal end 111 of channel guide 103.

FIGS. 22–49 disclose various components of an embodiment for implanting an implant (e.g., implant 900 of FIG. 49) into an intervertebral space. Generally, the system includes a set of differently sized rasps (e.g., see rasp 600 of FIGS. 25 and 26) for determining the implant size required to match an intervertebral space. The system also includes a set of differently sized cutting tools (e.g., see cutting instrument 510 of FIGS. 22–24) for cutting bone surrounding the intervertebral space. The size and shape of the cutting tool selected is determined by the size and shape of the rasp. Preferably, the cutting tool slides onto the rasp. Before or after cutting, the rasp can be manipulated to condition or roughen a portion of the site for the implant. Thereafter, the rasp and the cutting tool can be removed. Finally, the implant(s) is inserted into the space.

FIG. 22 is a top view and FIG. 23 a side view of another alternative embodiment of a bone cutting instrument 510 according to the invention. Instrument 510 has a proximal end 515 and a distal end 516 spaced along longitudinal axis X—X. At the proximal end 515 of shaft 517 there is a handle 518 for operating instrument 510. The handle 518 has a roughened area 519 that can be in the form of knurls, etchings, grooves, ridges, or other suitable patterns to enhance manual gripping of the handle 518. At the distal end 516, instrument 510 includes a first cutting edge 520, a second cutting edge 521, and third and fourth cutting edges 522 and 523. In the illustrated embodiment, cutting edges 520, 521, 522 and 523 are at the distal end of chamber 525. First, second, third, and fourth cutting edges 520, 521, 522 and 523 are beveled 520a, 521a, 522a, and 523a, respectively, to facilitate cutting and removal of bone. An internal hollow bore 527 extends from the proximal end 515 through the instrument 510 to the distal end 516 to receive a rasp 600 and to receive bone.

In the illustrated embodiment, elongated openings 550 and 551 extend through the handle 518 and shaft 517, respectively, of the instrument 510. As described later in the specification, opening 550 allows for alignment of the cutting instrument 510 with rasp 600. Opening 551 provides additional access to the internal bore 527 for cleaning the instrument and reduces the weight of the instrument.

FIG. 24 is a distal end-on view of instrument 510 showing that first and second cutting edges 520 and 521 define a height dimension $C_H$ and the cutting edges 522 and 523 define a width dimension $W_C$. The perimeter configuration of cutting edges 520, 521, 522, and 523 in FIG. 24 is a rectangular shape particularly suited for preparing a channel or implant bore between adjacent bones for insertion of a two-part implant having a configuration such as that of the implant 900 shown in FIG. 49.

Figure 49:
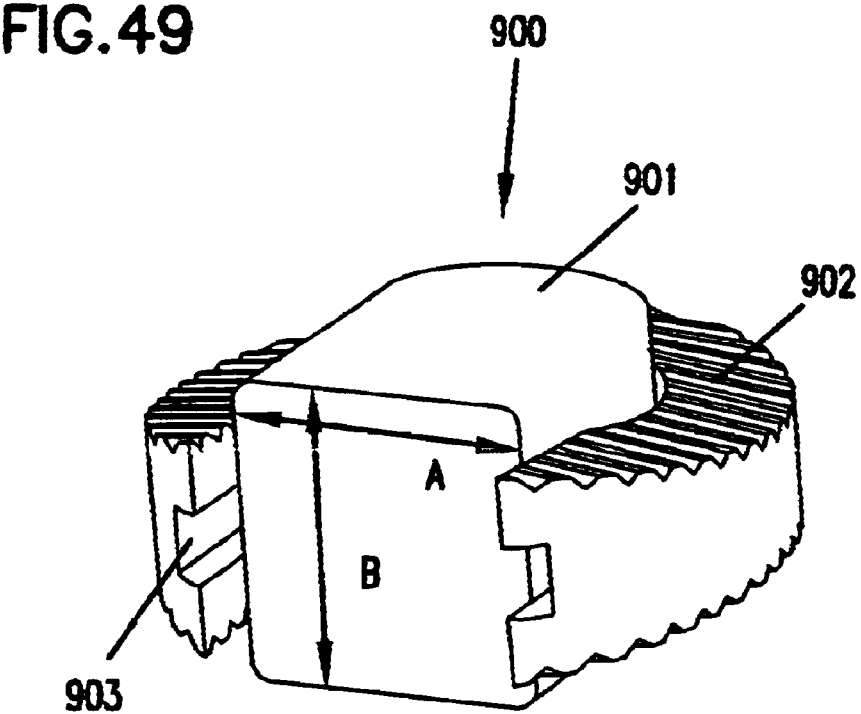
FIG. 49 is a perspective view of a two-part implant.

In the illustrated embodiment of FIG. 49, implant 900 is shown with growth component 901, such as cancellous bone, and support component 902, such as cortical bone. The growth component 901 has a similar size and shape as the distal end of the cutting instrument 510 (e.g., dimension A of growth component 901 corresponds to dimension $W_C$ of cutting instrument 510 and dimension B of growth component 901 corresponds to dimension $C_H$ of cutting instrument 510). Also, the rounded nose of the growth component 901 corresponds to the curvature of edges 520 and 521 of the cutting instrument 510. The support component 902 has a similar size and configuration as the rasp head (see for example FIGS. 25, 26). The support component 902 of the implant may be the same size as the rasp head, or it can be larger than the rasp head. The support component 902 of the implant can be about 0 mm to about 4 mm larger in height than the rasp head. The height dimension $C_H$ of the bone cutting instrument can be from about 0 mm to about 10 mm taller overall than the support component of the implant. It will be appreciated, however, that the perimeter configuration of cutting edges 520, 521, 522, and 523 can be square, circular, oval, etc., depending on the external configuration of the implant to be inserted into the channel. The length of the first and second cutting edges 520 and 521 can vary to correspond with the depth of the vertebrae.

To cut different sized channels, a set of bone cutting instruments 510 will be available which has instruments with incrementally different sizes of cutting edges 520, 521, 522, 523 corresponding to a particular size implant. For example, bone cutting instruments 510 having first and second cutting edges 520, 521 with different heights $C_H$ will be available to permit the surgeon to select a cutting edge height corresponding to a particular disc space height. In addition, it will be appreciated that the illustrated cutting edges 520 and 521 (and 522 and 523) are parallel. In alternative embodiments, cutting edges 520 and 521 (and 522 and 523) can form a converging or diverging taper.

Figure 25:
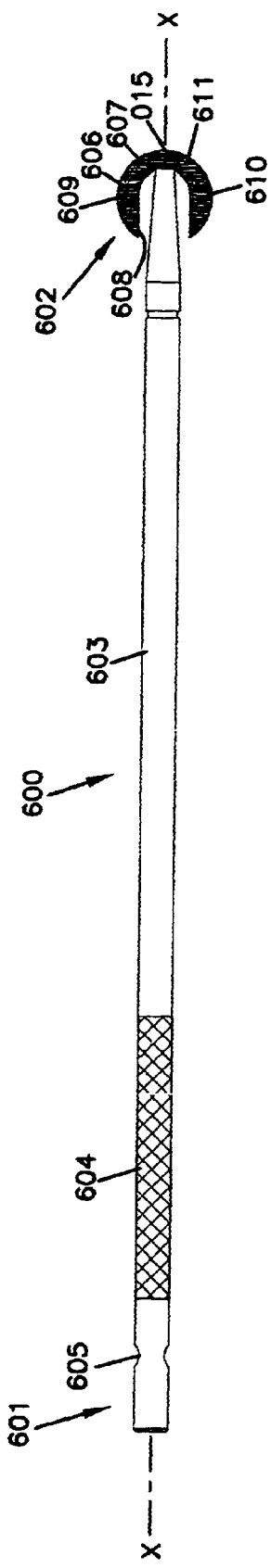
FIG. 25 is a top view of a rasp according to the invention.
Figure 26:
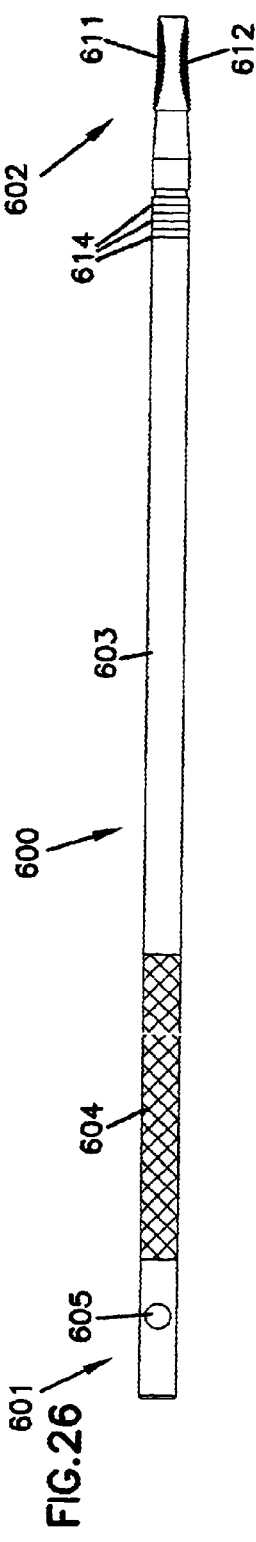
FIG. 26 is a side view of the rasp of FIG. 25.

FIG. 25 is a top view and FIG. 26 a side view of a rasp 600 according to one embodiment of the invention. The rasp 600 is inserted into the intervertebral space, and functions both as a trial sizer, i.e. for a particularly sized and shaped implant, and rasp. Rasp 600 has a proximal end 601 and a distal end 602 spaced along longitudinal axis X—X. At the proximal end 601 of shaft 603 there is a roughened area 604 that can be in the form of knurls, etchings, grooves, ridges, or other suitable patterns to enhance manual gripping of the shaft 603. An opening 605 for receiving a portion of an alignment pin extends transversely through the proximal end 601 of the shaft 603, and allows for alignment of the rasp with cutting instrument 510.

At the distal end 602, rasp 600 includes a rasp head 606. In the illustrated embodiment, rasp head 606 includes an outer wall 607, an inner wall 608 and has a generally "C-shaped" configuration with a first arm 609 continuous with a second arm 610. The inner wall 608 defines a pocket or receptacle which is sized to complement and receive the distal end of the cutting instrument 510. The first arm 609 and second arm 610 are spaced apart from the shaft 603. Rasp head 606 includes a first engaging surface 611 and a second engaging surface 612. In the illustrated embodiment, the first and second engaging surfaces 611, 612 have ridges 613.

Figure 27:
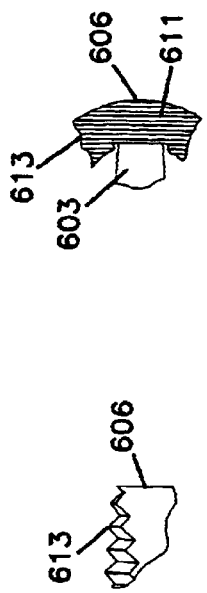
FIG. 27 is a proximal end-on view of the rasp of FIG. 25.

As illustrated best in FIG. 27, in this embodiment, rasp head 606 has a major height $H_M$ and minor height $H_m$. The taper from the major height to the minor height can be from about 0° to about 16°. The shape and configuration of the rasp head 606 corresponds to the shape and configuration of an implant. In one embodiment, the rasp head 606 corresponds in size and configuration with the support component 902 of a two-part implant 900. The space between the first and second arms 609, 610 of the rasp head 606 corresponds with the growth component 901 of the implant. It will be appreciated, however, that the configuration of the rasp head 606 can be square, rectangular, circular, oval, etc., depending on the configuration of the implant(s) to be inserted into the channel.

As a trial sizer, the rasp 600 provides a means for determining the appropriate size bone cutting instrument and implant to use for a particular implant site. Multiple rasps 600 are provided, with incrementally different sized, shaped, and/or tapered rasp heads 606 corresponding to different sized, shaped, and/or tapered implants. The surgeon inserts and removes the various rasps 600 and determines which one is the correct size for the intervertebral space. The ridges 613 on the upper and lower surfaces of the rasp head act as a rasp to condition the upper and lower surfaces of the channel between the vertebrae.

Proximal to the distal end 602, the shaft 603 of the rasp 600 also includes markings 614 at predetermined distances from the distal edge 615 of the rasp head. During use, markings 614 provide the surgeon with an indication of the depth of distal penetration of rasp 600 between adjacent bones.

In one embodiment, the rasp shaft 603 is slidably received within the internal bore 527 of the bone cutting instrument 510, with the opening 605 in the rasp shaft 603 accessible through the opening 550 in the bone cutting instrument handle 518. An alignment pin 700 (see FIGS. 30–39) is inserted through openings 550, 605 to align the rasp within the bone cutting instrument. When the alignment pin 700 is in place, the shaft 603 of the rasp rides within the opening 550 in the bone cutting instrument 510 to maintain rotational alignment and limit the axial movement to within a predetermined range corresponding to the length of opening 550. The alignment pin 700 also can function as a handle when the bone cutting instrument/rasp combination is forced between (e.g. hammered into) the adjacent bones to create the implant channel.

The alignment pin 700 has a handle 701, a collar 702, and a pin 703. The handle 701 can have a roughened surface that can be in the form of knurls, etchings, grooves, ridges, or other suitable patterns to enhance manual gripping of the handle 701. Alternatively, the handle 701 can be a shape that enhances manual gripping. In the illustrated embodiment, the handle 701 has indentations 704 to enhance manual gripping. The collar 702 is mounted to the handle 701 and the pin 703 is mounted to the collar 702. The collar 702 can be of any shape. In the illustrated embodiment, the collar 702 has a circumferential ridge 705. The ridge 705 has opposing flattened areas 706 that allow for unimpeded hammering of the bone cutting instrument and rasp while manually grasping the alignment pin.

Figure 40:
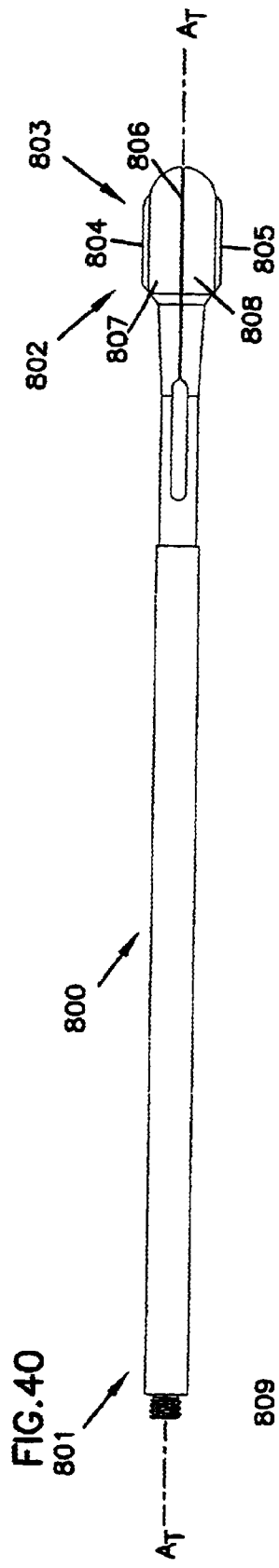
FIG. 40 is a top view of an implant insertion tool of the invention.
Figure 41:
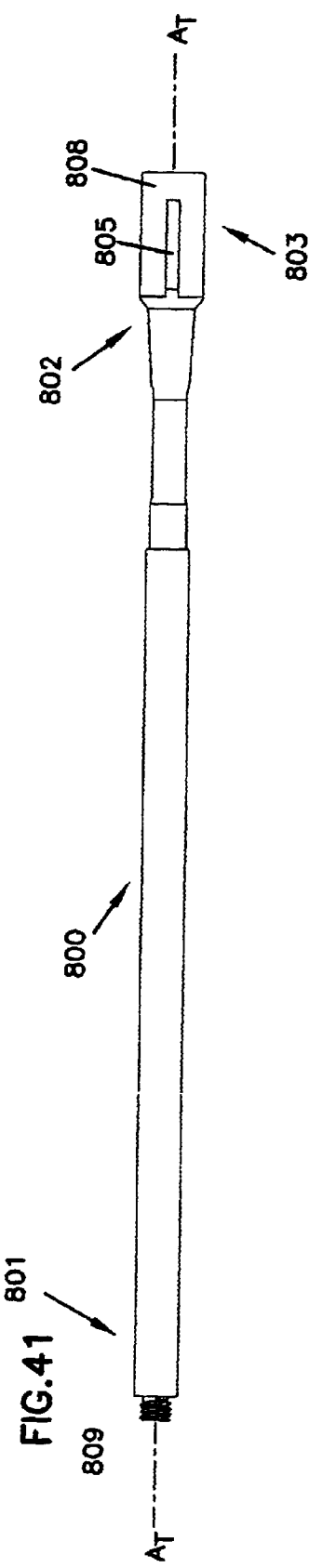
FIG. 41 is a side view of the implant insertion tool of FIG. 40.
Figure 43:
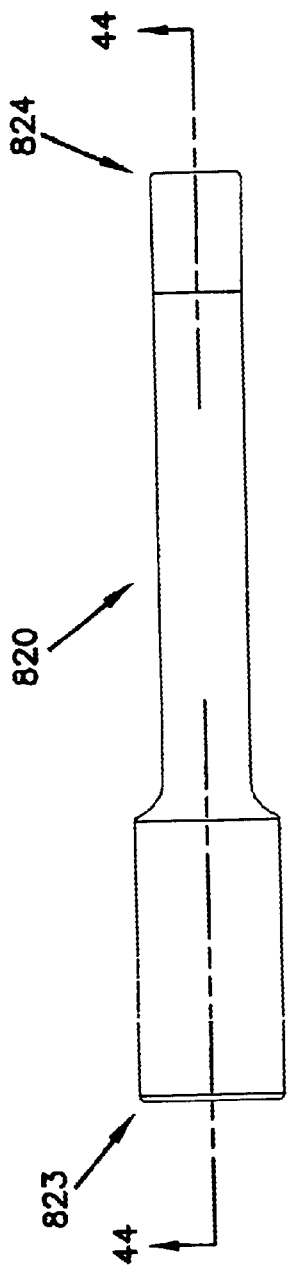
FIG. 43 is a side view of a sleeve of the invention.
Figure 44:
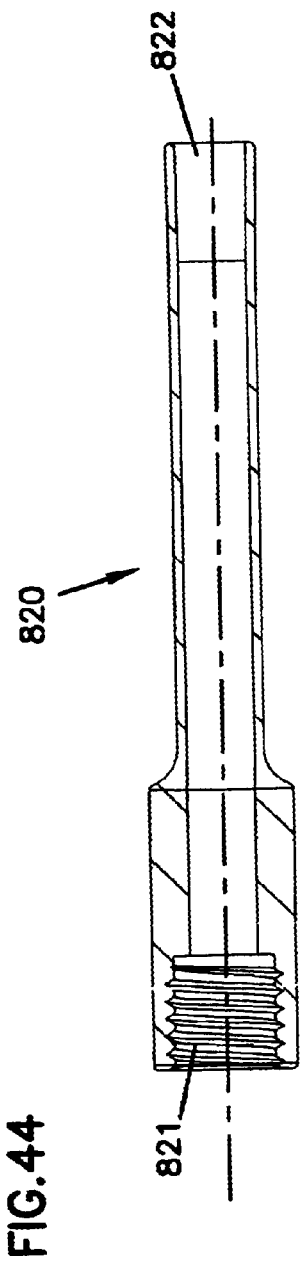
FIG. 44 is a side cross-sectional view of the sleeve of FIG. 43.
Figure 45:
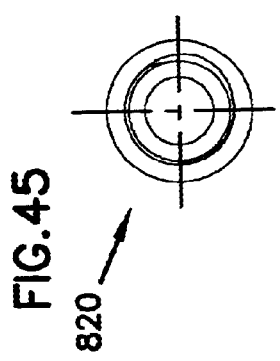
FIG. 45 is an end-on view of the sleeve of FIG. 43.

Once a channel is cut into adjacent bones, an implant or implants are inserted to fuse the adjacent bones and provide stability to the site. In one embodiment, a two part implant 900 such as that shown in FIG. 49 is used. The support component 902 is inserted into the channel, and then the growth component 901 is inserted. FIGS. 40 and 41 illustrate one embodiment of an implant insertion tool 800 suitable for use with embodiments of the bone cutting instrument 510 and rasp 600 of the invention. As illustrated, implant insertion tool 800 has a proximal end 801 and a distal end 802 having a working end 803. Working end 803 includes tabs 804 and 805 that fit cooperatively within grooves 903 of the support component 902 of an implant (see FIG. 49). In addition, the working end 803 includes a slot 806 that permits resilient/elastic arms 807 and 808 to flex or expand laterally away from axis $A_T$.

In a typical embodiment, arms 807 and 808 are spring biased to expand away (e.g., laterally) from axis $A_T$ in the normal, relaxed position. A sleeve 820 (FIGS. 43–45) can then be slid from the proximal end 801 of the insertion tool 800, over the slot 806, to force arms 807 and 808 towards (e.g. medially) axis $A_T$. That is, when the sleeve is advanced distally it brings arms 807 and 808 together towards axis $A_T$. In this position, the working end 803 of implant insertion tool 800 can be inserted into an implant. Similarly, where useful for additional control, tabs 804 and 805 can be inserted into grooves 903 of an implant. The sleeve can then be slid towards the proximal end to allow arms 807 and 808 to expand away from axis $A_T$ to provide friction holding of an implant on the working end 803. After placement of an implant, the sleeve can be slid distally to bring arms 807 and 808 back toward axis $A_T$ to remove implant insertion tool 800, leaving the implant in place. Other arrangements providing for expansion and contraction of arms 807, 808, relative to axis $A_T$ also are contemplated by this disclosure Thus, an implant can be mounted on the working end 803 of implant insertion tool 800 allowing the surgeon to manipulate an implant via tool 800 into a suitable position at the fusion site.

Figure 46:
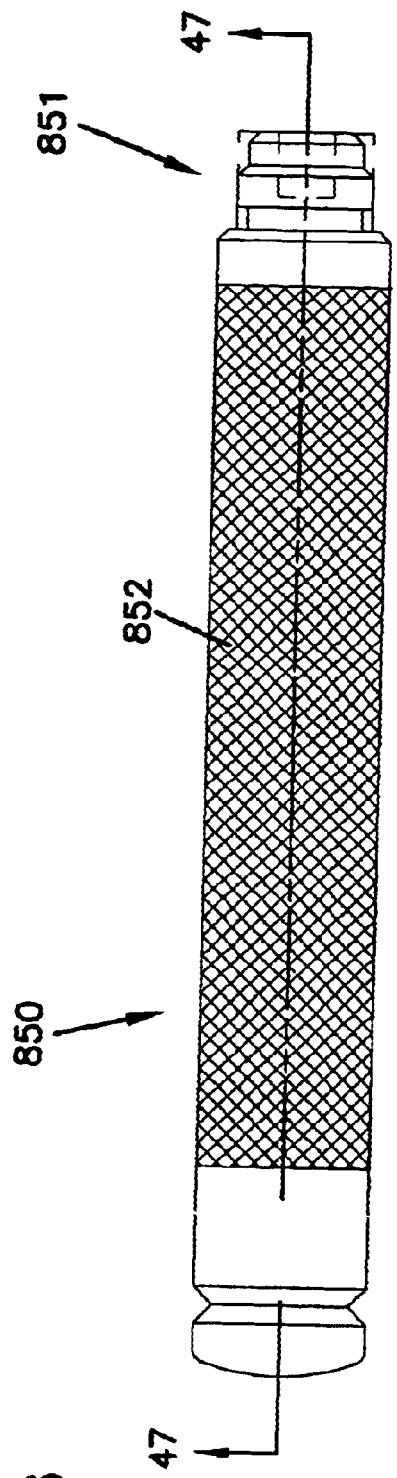
FIG. 46 is a top view of an insertion tool handle of the invention.
Figure 47:
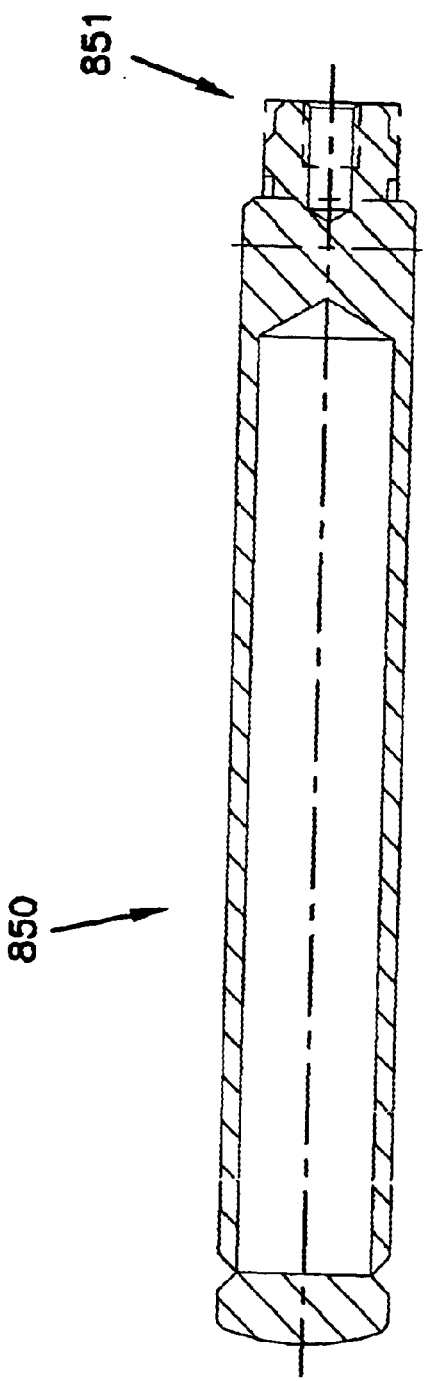
FIG. 47 is a cross-sectional view of the handle of FIG. 46.
Figure 48:
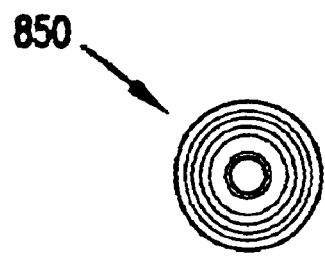
FIG. 48 is a cross-sectional view of the handle of FIG. 46.

In one embodiment, the implant insertion tool 800 includes a sleeve 820 (FIGS. 43–45) and a handle 850 (FIGS. 46–48). In the illustrated embodiment, the insertion tool 800 has a threaded region 809 at the proximal end 801. The threaded region 809 mates with the distal end 851 of the handle 850. The handle has a roughened area 852 that can be in the form of knurls, etchings, grooves, ridges, or other suitable patterns to enhance manual gripping of the handle 850. In one embodiment, the distal end 851 of the handle 850 has exterior threading to match internal threading 821 on a sleeve 820.

The sleeve 820 is hollow and has a bore 822 extending from the proximal end 823 to the distal end 824, and which is sized to fit over the proximal end 801 of the implant insertion tool 800, and to threadibly advance, i.e. distally, over slot 806, to force arms 807 and 808 towards axis $A_T$.

II. Methods

The instruments of the invention can be used to prepare a channel of a selected configuration between adjacent bones, and to insert an implant or implants into the prepared channel. For exemplary purposes, the methods of the invention will be described with respect to preparing a channel between adjacent vertebral bodies. However, it will be appreciated that the principles and methods can also be applied to preparing a channel between other bones.

The present invention will first be described with reference to use in a posterior approach. In a posterior approach, a surgeon seeks access to the spine through the back of the patient. An alternative approach is the lateral approach where the patient is on his side. Another alternative approach is an anterior approach where the surgeon seeks access to the spine through the abdomen of a patient. The approaches can be done through an open or laparoscopic procedure.

Figure 21:
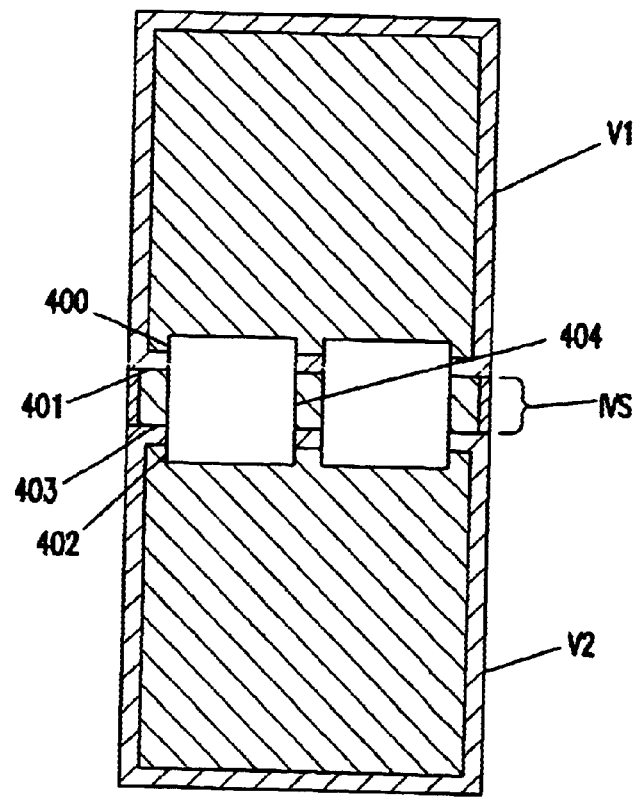
FIG. 21 is a diagrammatical illustration of adjacent vertebrae having channels for receiving implants and prepared according to the invention.

With reference to FIG. 21, once a surgeon has identified two vertebrae that are to be fused, e.g., lumbar vertebrae $V_1$ and $V_2$, the surgeon determines the size of the desired implant and the desired amount of distraction of the intervertebral disc space IVS required before placement of the implant.

Exposure of the intervertebral disc can be obtained through any suitable technique known in the art. Preferably, the facet of the vertebrae is removed in as limited amount as possible to permit insertion of the implant site preparation instruments and the implant. Single or multiple implants can be used. If a single implant is used, the implant is typically positioned centrally within the lateral margins of the disc space. If a pair of implants is used, they are positioned on either side of the midline of the vertebrae and within the lateral margins of the disc space. If a single implant is used, the transverse (width) dimension of the implant will generally be greater than the transverse dimension of a single one of a pair of implants. A single implant is more likely to be used in a lateral or anterior approach than a posterior approach due to restrictions on the amount of lateral retraction that can be applied to the spinal cord.

Figure 28:
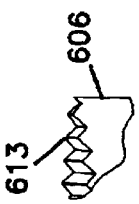
FIG. 28 is an enlarged partial perspective view of the teeth on the rasp head of the invention.
Figure 29:
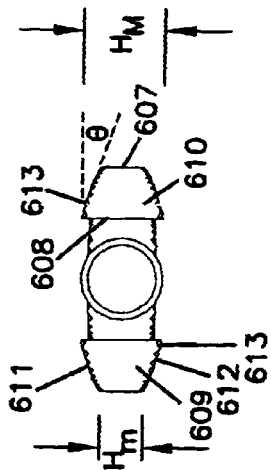
FIG. 29 is an enlarged partial top view of the rasp head of FIG. 25.
Figures 30, 31, 32:
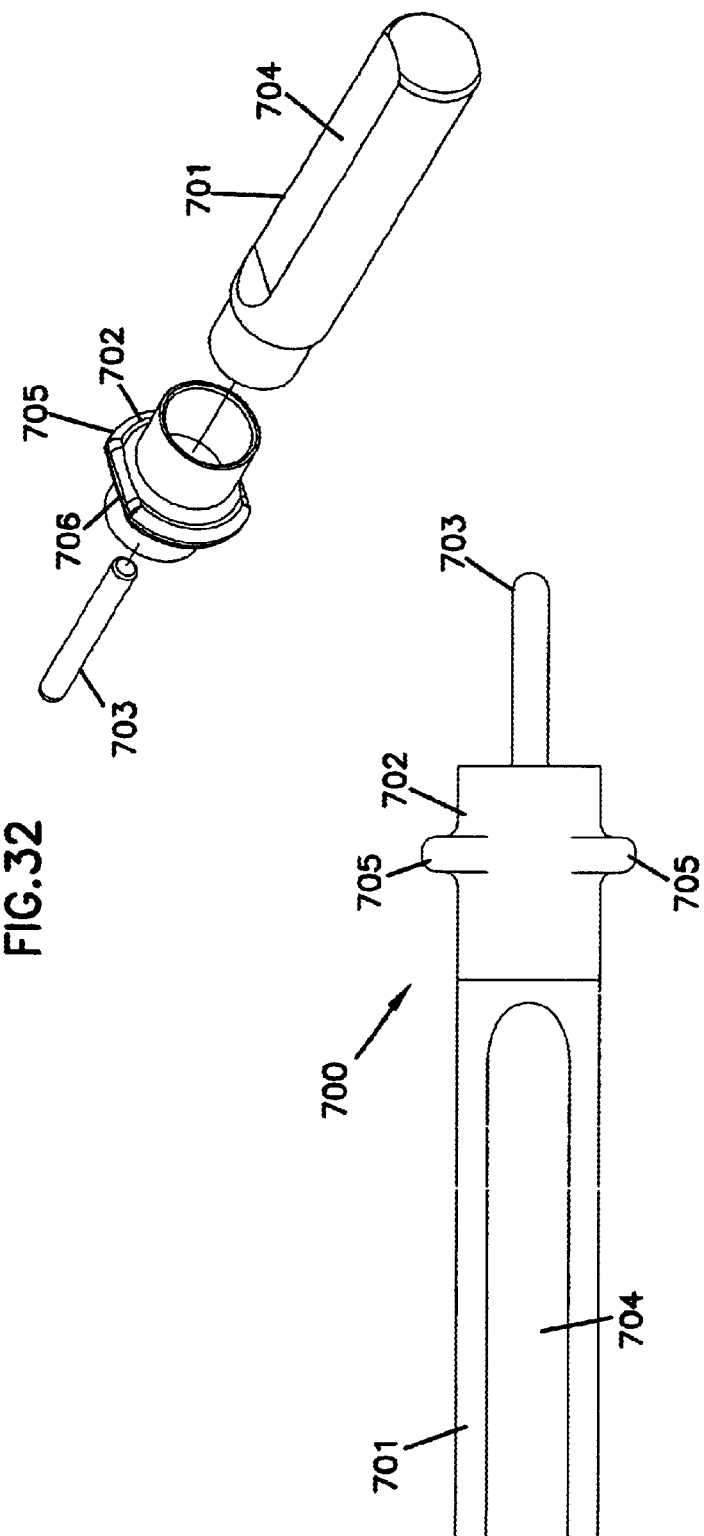
FIG. 30 is a top view of an alignment pin of the invention.
FIG. 31 is a side view of the alignment pin of FIG. 30.
FIG. 32 is an exploded perspective view of the alignment pin of FIG. 30.
Figure 33:
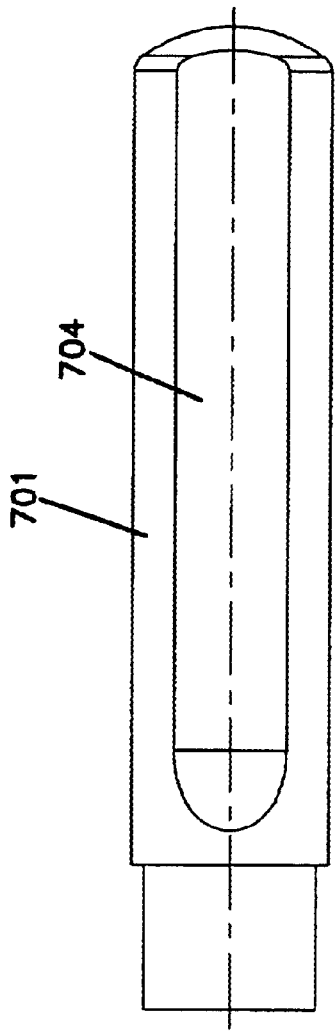
FIG. 33 is a top view of the handle of the alignment pin of the invention.
Figure 34:
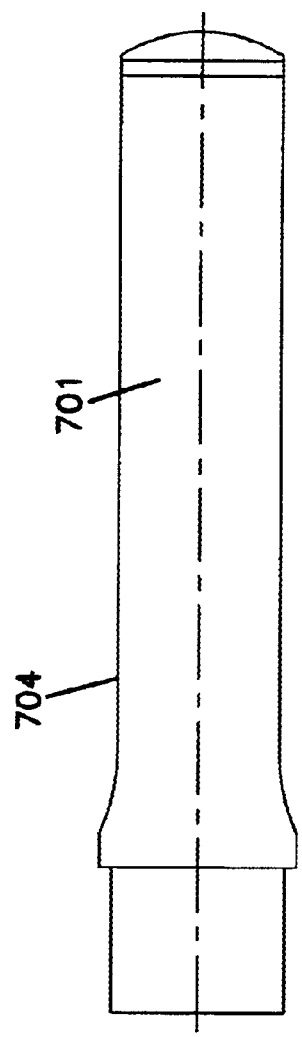
FIG. 34 is a side view of the handle of FIG. 33.
Figure 35:
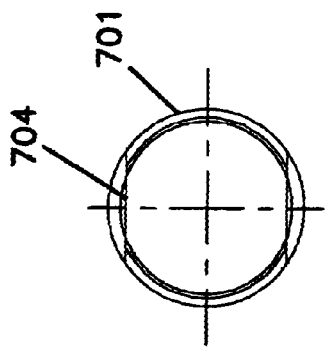
FIG. 35 is a distal end-on view of the handle of FIG. 33.
Figure 36:
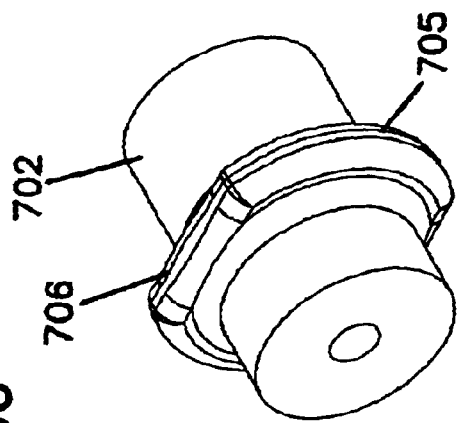
FIG. 36 is a perspective view of a collar of the alignment pin of the invention.
Figure 39:
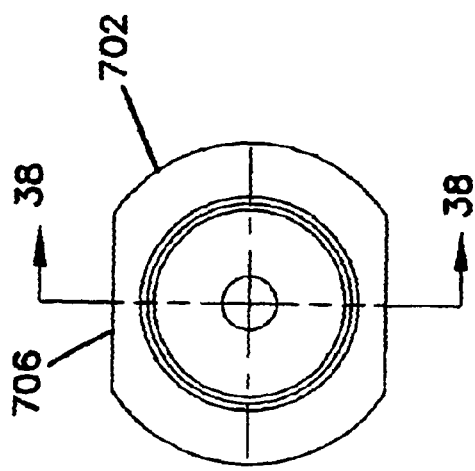
FIG. 39 is an end-on view of the collar of FIG. 36.
Figure 37:
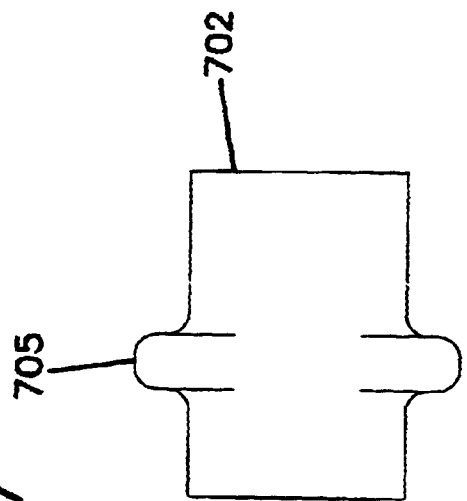
FIG. 37 is a top view of the collar of FIG. 36.
Figure 38:
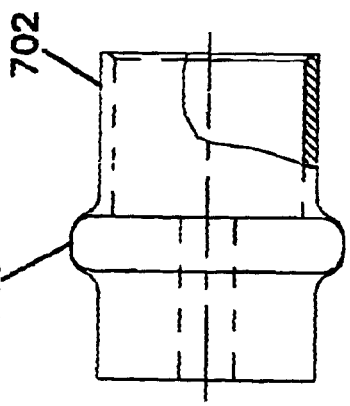
FIG. 38 is a side view of the collar of FIG. 36.
Figure 42:
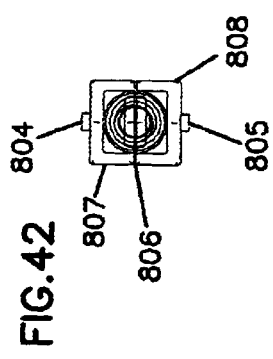
FIG. 42 is a distal end-on view of the implant insertion tool of FIG. 40.

Continuing with the posterior approach to lumbar vertebrae $V_1$ and $V_2$, after lateral retraction of the cauda equina, a partial or full discectomy can be performed using known methods, being careful to maintain as much of the annulus as possible. A bone cutting instrument 100 (including mandrels 104, 105) having paddles with a major height dimension $P_{H1}$ approximating the desired disc space height is passed into a first side of the intervertebral disc space between adjacent vertebrae $V_1$ and $V_2$. In one embodiment, a distraction spacer, such as shown in FIG. 28 of U.S. Pat. No. 5,489,307, or similar device, can be used to maintain distraction of the disc space on a second side (i.e., contralateral to the first side being prepared) of the vertebral bodies $V_1$ and $V_2$. If a distraction spacer is used, after preparation of the first side, the implant can be inserted into the channel prior to preparation of the channel on the second side. Alternatively, after preparing the channel on the first side, the bone cutting instrument can be removed and the cauda equina retracted over the first side and the channel on the second side prepared before inserting the implants.

During insertion of the paddles 120, 121, of bone cutting instrument 100 (FIG. 5), it may be advantageous to initially insert a paddle having a smaller than desired paddle height dimension $P_{H1}$ and sequentially insert instruments having increasing paddle heights $P_{H1}$ until the desired disc space height is achieved. Once the tapered distal ends of the paddles are inserted into the disc space, the proximal ends of channel guide 103 and mandrels 104 and 105 can be tapped (i.e., typically as a single unit), for example, with an orthopedic hammer, to advance the paddles into the disc space until the shoulders 130, 131 abut the posterior surfaces of the vertebral bodies.

The first mandrel 104 can then be removed and replaced with bone chisel 106 that is passed along track 112. The proximal end 301 of chisel 106 is then tapped into first vertebrae $V_1$ to cut a first notch 400 into endplate 401. Chisel 106 is then removed and can be replaced by first mandrel 104. Second mandrel 105 can then be removed and replaced with bone chisel 106 that is passed along track 113 into second vertebrae $V_2$ to cut a first notch 402 into endplate 403 of second vertebrae $V_2$. The bone channel guide 103 with mandrel 104 and bone chisel 106 can then be removed leaving channel 404 defined by notches 400 and 402 as indicated with broken lines in FIG. 21. An implant, such as a rectangular bone plug can then be inserted into channel 404 on the first side and the above procedure repeated on the second side. If the bone cutting instrument has a circular cutting edge, and a threaded implant is to be used, the channel formed can be threadedly tapped using known tapping instrumentation.

In an alternative embodiment, after lateral retraction of the cauda equina and discectomy, a bone cutting instrument 10 (FIGS. 1–3) having a preselected paddle height $P_H$ can be inserted into the first side of the intervertebral disc space. As described above, cutting instruments 10 having paddles of increasingly greater paddle height dimension $P_H$ can be sequentially inserted into the disc space until the appropriate disc height is established. A distraction spacer may be used on the contralateral side as previously described. After the tapered distal ends 20a, 21a of paddles 20 and 21 having the appropriate height dimension $P_H$ are inserted into the intervertebral disc space (IVS), the bone cutting instrument 10 is advanced until bone cutting surface 23 contacts the posterior surfaces of vertebrae $V_1$ and $V_2$. At this point, without removing the bone cutting instrument, the proximal end 15 of instrument 10 can be tapped to further advance cutting edge 23 to simultaneously remove bone from the endplates of the adjacent vertebrae $V_1$ and $V_2$. Bone and disc material cut by cutting surface 23 will pass into chamber 25 and out opening 24. Advancement of cutting instrument 10 into the intervertebral disc space is continued until the paddles (or cutting edge) have reached a predetermined depth that can be indicated by marks 30. Alternatively, the depth to which cutting instrument 10 is inserted into the disc space can be determined by visualization methods such as x-ray, MRI, CT scan, etc.

Once the appropriate depth has been reached, bone cutting instrument 10 is removed and any debris remaining in the channel can be removed using a rongeur, osteotome, forceps, etc. If a threaded implant is to be used, the channel formed by cutting instrument 10 can be tapped using known methods for tapping an implant bore. If a second implant site is to be prepared, the first implant can be inserted prior to preparation of the second implant site or both implants inserted after both implant sites are prepared.

Again with reference to FIG. 21, once a surgeon has identified two vertebrae that are to be fused, e.g., lumbar vertebrae $V_1$ and $V_2$, the surgeon can use the rasp to determine the size of the desired implant and the desired amount of distraction of the intervertebral disc space (IVS) required before placement of the implant. Exposure of the intervertebral disc can be obtained through any suitable technique known in the art, such as by using a distractor. The distractor is inserted between the adjacent bone surfaces, and a rasp is passed through the adjacent bone surfaces to space the bone surfaces apart a predetermined distance. The distractor provides an exposure window through which the bone cutting instrument, rasp, and implant inserting tool with the implant can be inserted, as is more thoroughly described in U.S. Pat. No. 6,224,599 to Baynham, which is incorporated herein by reference.

The surgeon can determine the size of the desired implant 900 and can select the appropriately sized bone cutting instrument 510, and implant inserting tool 800 using a series of rasps 600. The rasp 600 functions as a trial sizer in that the rasp heads 606 correspond to various incremental implant sizes and shapes. The dimensions of the rasp head 606 are proportional to the dimensions of the bone cutting instrument 510, implant inserting tool 800 and the implant 900. Once a rasp 600 is found that corresponds to the size of the intervertebral space for a particular patient between particular vertebrae, the rasp 600 can be moved into and out of the space to prepare the vertebrae for receiving the implant 900. The roughened surfaces 611, 612 on the rasp head 606 function as a rasp to provide a more uniform and osteoconductive/osteoinductive site for the implant.

Leaving the rasp 600 in place, the surgeon selects the appropriately sized bone cutting instrument 510 and slides it over the rasp shaft 603, aligning the openings 550, 605 in the proximal shafts of the bone cutting instrument and rasp. The alignment pin 700 is inserted into the openings to maintain the alignment, and the bone cutting instrument 510 is forced, e.g. forced, into place. The openings 550, 605 in the shafts of the bone cutting instrument and rasp provide a stop when aligned with the alignment pin 700 to prevent the bone cutting instrument 510 from cutting too deep into the intervertebral space. The inner surface 608 of the rasp head 606 also acts as a stop for the third and fourth cutting edges 522, 523 of the bone cutting instrument 510.

Once the channel has been cut, a slap hammer can be attached to the shaft 517 of the bone cutting instrument 510 to remove the instrument and the rasp 600. The appropriately sized support component 902 of the implant 900 is positioned on the insertion tool 800 with the sleeve 820 in the proximal position, and the implant is inserted into the prepared channel. The sleeve 820 is then advanced distally to force the arms 807, 808 of the insertion tool toward one another to release the implant. If a two-part implant is used, the second part of the implant (growth component 901) is then inserted.

From the foregoing detailed description and exemplary embodiments, it will be evident that modifications and variations can be made in the devices and methods of the invention without departing from the spirit or scope of the invention. Therefore, it is intended that all modifications and variations not departing from the spirit of the invention come within the scope of the claims appended hereto.

What is claimed is:

1. A bone cutting instrument comprising:
   a proximal end and a distal end spaced apart along a longitudinal axis of the instrument;
   first and second cutting edges at the distal end, the first and second cutting edges being diametrically opposed; and
   third and fourth cutting edges at the distal end, the third and fourth cutting edges being diametrically opposed and adjacent the first and second cutting edges; wherein the first, second, third, and fourth cutting edges define an interior void, and the first and second cutting edges extend distally beyond the third and fourth cutting edges; wherein the first and second cutting edges are radiused.

2. The bone cutting instrument according to claim 1 wherein a relationship of the first, second, third, and fourth cutting edges defines a parallelogram.

3. The bone cutting instrument according to claim 1 further comprising a shaft disposed between the proximal and distal ends, the shaft comprising an elongated opening at the proximal end, substantially perpendicular to the longitudinal axis.

4. The bone cutting instrument according to claim 3 further comprising a hollow bore extending from the proximal end to the distal end.

5. The bone cutting instrument of claim 1 further including indicator markings to determine depth of cutting.

6. A bone cutting instrument comprising:
   a proximal end and a distal end spaced apart along a longitudinal axis of the instrument;
   a hollow bore extending from the proximal end to the distal end;
   first and second cutting edges at the distal end, the first and second cutting edges being diametrically opposed and radiused; and
   third and fourth cutting edges at the distal end, the third and fourth cutting edges being diametrically opposed and adjacent the first and second cutting edges; wherein the first, second, third, and fourth cutting edges define an interior void; wherein a relationship of the first, second, third, and fourth cutting edges defines a parallelogram, and the first and second cutting edges extend distally beyond the third and fourth cutting edges.

7. A bone cutting instrument comprising:

a proximal end and a distal end spaced apart along a longitudinal axis of the instrument;

first and second cutting edges at the distal end, the first and second cutting edges being diametrically opposed; and third and fourth cutting edges at the distal end, the third and fourth cutting edges being diametrically opposed and adjacent the first and second cutting edges; wherein the first second, third, and fourth cutting edges define an interior void, wherein the first and second cutting edges have a convex curvature extending between the third and fourth cutting edges, and the first and second cutting edges extend distally beyond the third and fourth cutting edges.

8. The bone cutting instrument of claim 7 further comprising a hollow bore extending from the proximal end to the distal end.

9. The bone cutting instrument of claim 7 wherein a relationship of the first, second, third, and fourth cutting edges defines a parallelogram.

* * * * *

UNITED STATES PATENT AND TRADEMARK OFFICE
CERTIFICATE OF CORRECTION

PATENT NO. : 6,635,060 B2
DATED : October 21, 2003
INVENTOR(S) : Hanson et al.

It is certified that error appears in the above-identified patent and that said Letters Patent is hereby corrected as shown below:

Column 17,
Line 10, "first second, third" should read -- first, second, third --
Line 11, "interior void, wherein" should read -- interior void; wherein --

Signed and Sealed this

Thirty-first Day of August, 2004

JON W. DUDAS
*Director of the United States Patent and Trademark Office*